US010252958B2

(12) United States Patent
Xu et al.

(10) Patent No.: US 10,252,958 B2
(45) Date of Patent: Apr. 9, 2019

(54) PROCESS FOR XYLENE PRODUCTION WITH ENERGY OPTIMIZATION

(71) Applicant: SAUDI ARABIAN OIL COMPANY, Dhahran (SA)

(72) Inventors: Qi Xu, Dhahran (SA); Raed Abudawoud, Khobar (SA); Ahmad A. Jazzar, Riyadh (SA); Zhonglin Zhang, Dhahran (SA)

(73) Assignee: SAUDI ARABIAN OIL COMPANY (SA)

( * ) Notice: Subject to any disclaimer, the term of this patent is extended or adjusted under 35 U.S.C. 154(b) by 0 days.

(21) Appl. No.: 16/173,412

(22) Filed: Oct. 29, 2018

(65) Prior Publication Data
US 2019/0062241 A1 Feb. 28, 2019

Related U.S. Application Data

(63) Continuation-in-part of application No. 16/018,394, filed on Jun. 26, 2018, which is a continuation of
(Continued)

(51) Int. Cl.
C07C 15/08 (2006.01)
C10G 45/72 (2006.01)
(Continued)

(52) U.S. Cl.
CPC .............. C07C 15/08 (2013.01); C07C 6/126 (2013.01); C10G 45/44 (2013.01); C10G 45/46 (2013.01);
(Continued)

(58) Field of Classification Search
CPC ....... C07C 15/08; C07C 5/2729; C07C 6/123; C07C 7/005; C07C 7/13; C07C 7/14;
(Continued)

(56) References Cited

U.S. PATENT DOCUMENTS 4,013,734 A 3/1977 Kim
4,127,471 A 11/1978 Suggitt et al.
(Continued)

FOREIGN PATENT DOCUMENTS

EP 0816311 A1 1/1998
WO 0010944 A1 3/2000
(Continued)

OTHER PUBLICATIONS

Alario, et al., "Para-xylene Manufacturing: Catalytic Reactions and Processes," 3 Catalytic Science Series: Zeolites for Cleaner Technologies (2002), 189-207.
(Continued)

Primary Examiner — Sharon Pregler
(74) Attorney, Agent, or Firm — Bracewell LLP; Constance Gall Rhebergen

(57) ABSTRACT

A method for producing xylenes from a heavy reformate feed includes the steps of introducing the heavy reformate feed and a hydrogen feed to a dealkylation reactor, reacting the heavy reformate feed with the hydrogen gas in the presence of the dealkylation catalyst in the dealkylation reactor to produce a dealkylation effluent, introducing the dealkylation effluent to a splitter unit, separating the dealkylation effluent into a light gas stream, a toluene stream, a benzene stream, a C9 aromatics stream, a C10+ aromatics stream, and a mixed xylene stream in the splitter unit, introducing the toluene stream, the C9 aromatics stream, and a hydrogen stream into a transalkylation reactor, reacting the toluene stream and the C9 aromatics stream in the presence of the transalkylation catalyst to produce a transalkylation effluent, introducing the transalkylation effluent to the splitter unit, and separating the transalkylation effluent in the splitter unit.

18 Claims, 12 Drawing Sheets

Related U.S. Application Data application No. 15/606,600, filed on May 26, 2017, now Pat. No. 10,035,742.

(51) Int. Cl.
| | |
|---|---|
| *C10G 65/04* | (2006.01) |
| *C10G 47/00* | (2006.01) |
| *C07C 6/12* | (2006.01) |
| *C10G 45/46* | (2006.01) |
| *C10G 45/44* | (2006.01) |

(52) U.S. Cl.
CPC .............. *C10G 45/72* (2013.01); *C10G 47/00* (2013.01); *C10G 65/043* (2013.01); *B01J 2219/00027* (2013.01); *B01J 2219/00051* (2013.01); *C10G 2400/30* (2013.01)

(58) Field of Classification Search
CPC ........... C07C 2/862; C07C 2/864; C07C 4/14; C07C 5/2732; C07C 5/277; C07C 6/04; C07C 6/06; C07C 7/04; C07C 7/12; B01J 19/24; B01J 19/2445; B01J 19/245; B01J 2219/24
See application file for complete search history.

(56) References Cited

U.S. PATENT DOCUMENTS

| | | | |
|---|---|---|---|
| 4,172,813 | A | 10/1979 | Bertolacini et al. |
| 4,310,715 | A | 1/1982 | Dorawala et al. |
| 5,004,854 | A | 4/1991 | Yan |
| 5,030,787 | A | 7/1991 | Absil et al. |
| 5,763,720 | A | 6/1998 | Buchanan et al. |
| 5,847,256 | A | 12/1998 | Ichioka et al. |
| 5,866,741 | A | 2/1999 | Wu et al. |
| 5,942,651 | A | 8/1999 | Beech, Jr. et al. |
| 5,952,536 | A | 9/1999 | Nacamuli et al. |
| 6,096,938 | A | 8/2000 | Ghosh |
| 6,204,422 | B1 | 3/2001 | Tsutsui et al. |
| 6,359,184 | B1 | 3/2002 | Kato et al. |
| 6,706,937 | B2 | 3/2004 | Mao et al. |
| 7,288,687 | B1 | 10/2007 | Frey et al. |
| 7,544,849 | B2 | 6/2009 | Boldingh et al. |
| 7,563,358 | B2 | 7/2009 | Stavens et al. |
| 7,663,010 | B2 | 2/2010 | Levin |
| 7,727,490 | B2 | 6/2010 | Zhou |
| 8,071,828 | B2 | 12/2011 | Cao et al. |
| 8,084,657 | B2 | 12/2011 | Kong et al. |
| 8,183,424 | B2 | 5/2012 | Levin et al. |
| 8,198,502 | B2 | 6/2012 | Bresler et al. |
| 8,431,758 | B2 | 4/2013 | Frey et al. |
| 8,822,747 | B2 | 9/2014 | Corradi et al. |
| 9,000,247 | B2 | 4/2015 | Abudawoud |
| 9,249,068 | B2 | 2/2016 | Tinger et al. |
| 9,295,970 | B1 | 3/2016 | Tinger et al. |
| 9,302,953 | B2 | 4/2016 | Molinier et al. |
| 9,469,579 | B2 | 10/2016 | Molinier et al. |
| 2005/0197518 | A1 | 9/2005 | Miller et al. |
| 2007/0203376 | A1 | 8/2007 | Negiz et al. |
| 2008/0021253 | A1 | 1/2008 | Corma Canos et al. |
| 2009/0112034 | A1 | 4/2009 | Levin |
| 2012/0024755 | A1 | 2/2012 | Beech, Jr. et al. |
| 2012/0083638 | A1 | 4/2012 | Boldingh et al. |
| 2013/0165719 | A1 | 6/2013 | Negiz et al. |
| 2014/0100402 | A1 | 4/2014 | Gawlik et al. |
| 2015/0094508 | A1 | 4/2015 | Corradi et al. |
| 2015/0166435 | A1 | 6/2015 | Serban et al. |
| 2016/0185686 | A1 | 6/2016 | Molinier et al. |
| 2017/0152198 | A1* | 6/2017 | Colling .................. C10G 47/00 |

FOREIGN PATENT DOCUMENTS

| | | |
|---|---|---|
| WO | 2004056945 A1 | 7/2004 |
| WO | 2007137017 A1 | 11/2007 |
| WO | 2008094255 A1 | 8/2008 |
| WO | 2012006039 A2 | 1/2012 |
| WO | 2013158956 A1 | 10/2013 |

OTHER PUBLICATIONS

Commissaris, Scott E.; "UOP Parex Process", Handbook of Petroleum Refining Processes Third Edition, 2004, Chapter 2.6, pp. 2.47-2.53.

International Search Report and the Written Opinion for International Application No. PCT/US2013/037304 dated Jul. 4, 2013; pp. 1-9.

International Search Report and Written Opinion for International Application No. PCT/US2018/012129; International Filing Date Jan. 3, 2018; Report dated Apr. 24, 2018 (pp. 1-14).

International Search Report and Written Opinion for International Application No. PCT/US2018/032874; Report dated Jul. 5, 2018; 13 pgs.

Johnson, James A.; "Aromatics Complexes", Handbook of Petroleum Refining Processes Third Edition, 2004, Chapter 2.1, pp. 2.3-2.11.

Negiz, Antoine and Stoodt, Thomas J.; "UOP Tatoray Process", Handbook of Petroleum Refining Processes Third Edition, 2004, Chapter 2.7, pp. 2.55-2.63.

Silady, Ptrick J.; "UOP Isomar Process", Handbook of Petroleum Refining Processes Third Edition, 2004, Chapter 2.5, pp. 2.39-2.46.

* cited by examiner

PROCESS FOR XYLENE PRODUCTION WITH ENERGY OPTIMIZATION

CROSS REFERENCE TO RELATED APPLICATIONS

This application is a continuation-in-part of U.S. patent application Ser. No. 16/018,394 filed on Jun. 26, 2018, which claims priority from U.S. patent application Ser. No. 15/606,600 filed on May 26, 2017, issued on Jul. 31, 2018 as U.S. Pat. No. 10,035,742. For purposes of United States patent practice, this application incorporates the contents of both Non-Provisional Applications by reference in their entirety.

TECHNICAL FIELD

Disclosed are methods and systems for production of xylenes. Specifically, disclosed are methods and systems for production of xylenes from heavy aromatics.

BACKGROUND

Heavy reformate can include greater than 90 percent by weight (wt %) aromatics with eight or more carbon atoms in the aromatic compound. Of the aromatics, less than or equal to 10 wt % can be xylenes. In past practice, the heavy reformate was blended into the gasoline stream. However, blending is becoming more difficult due to more stringent regulations on the aromatics content in gasoline.

Para-xylene (p-xylene) is experiencing a market growth rate of demand. Consequently, the conversion of heavy aromatics to p-xylene provides a valuable product stream.

SUMMARY

Disclosed are methods and systems for production of xylenes. Specifically, disclosed are methods and systems for production of xylenes from heavy aromatics.

In a first aspect, a method for producing mixed xylenes from a heavy reformate feed is provided. The method includes the steps of introducing the heavy reformate feed to a feed exchanger to produce a hot feed stream, where the feed exchanger increases the temperature of the heavy reformate feed, where the heavy reformate includes aromatic hydrocarbons with nine or more carbon atoms (C9+ aromatics), where the hydrogen feed includes hydrogen gas, mixing the hot feed stream and a hydrogen feed to produce a mixed feed, increasing a temperature of the mixed feed in a feed-effluent exchanger to produce a hot mixed feed, where a temperature of the hot mixed feed is between 324 deg C. and 344 deg C., increasing the temperature of the hot mixed feed in a feed fired heater to produce a hot reactor feed, where a temperature of the hot reactor feed is between 380 deg C. and 400 deg C., introducing the hot reactor feed to a dealkylation reactor, where the dealkylation reactor includes a dealkylation catalyst, reacting the heavy reformate feed with the hydrogen gas in the presence of the dealkylation catalyst in the dealkylation reactor to produce a dealkylation effluent, where the dealkylation reactor is at a dealkylation temperature, where the dealkylation reactor is at a dealkylation pressure, where the dealkylation reactor has a liquid hourly space velocity, reducing a temperature of the dealkylation effluent in the feed-effluent exchanger to produce a cooled effluent stream, where a temperature of the cooled effluent stream is between 115 deg C. and 145 deg C., reducing the temperature of the cooled effluent in an effluent-separator exchanger to produce an effluent stream, where a temperature of the effluent stream is between 80 deg C. and 110 deg C., reducing the temperature of the effluent stream in an effluent cooler to produce a mixed effluent stream, where a temperature of the mixed effluent stream is between 38 deg C. and 47 deg C., separating the mixed effluent stream in an effluent separator to produce a produced hydrogen and a separated effluent, where the produced hydrogen includes hydrogen, increasing a temperature of the separated effluent in the effluent-separator exchanger to produce a dealkylation splitter feed, where a temperature of the dealkylation splitter feed is between 100 deg C. and 130 deg C., introducing the dealkylation splitter feed to a splitter unit, where the dealkylation effluent includes light gases, toluene, benzene, mixed xylenes, and C9+ aromatics, separating the dealkylation effluent into a light gas product, a toluene stream, a benzene stream, a C9 aromatics stream, a C10+ aromatics stream, and a mixed xylene stream in the splitter unit, where the light gas stream includes light hydrocarbons and hydrogen, where the toluene stream includes toluene, where the benzene stream includes benzene, where the mixed xylene stream includes mixed xylenes, where the C9 stream includes C9 aromatics, where the C10+ aromatics stream includes C10+ aromatics, mixing the toluene stream, the C9 aromatics stream, and a hydrogen stream in a mixer to produce a mixed transalkylation feed, increasing a temperature of the mixed transalkylation feed in a C9-effluent heater to produce a hot transalkylation feed, where a temperature of the hot transalkylation feed is between 330 deg C. and 390 deg C., increasing the temperature of the hot transalkylation feed in a transalkylation fired heater to produce a transalkylation feed, where a temperature of the transalkylation feed is between 380 deg C. and 400 deg C., introducing the transalkylation feed to a transalkylation reactor, where the transalkylation reactor includes a transalkylation catalyst, where the hydrogen stream includes hydrogen gas, reacting the toluene stream and the C9 aromatics stream in the presence of the transalkylation catalyst to produce a transalkylation effluent, where the transalkylation reactor is at a transalkylation temperature, where the transalkylation reactor is at a transalkylation pressure, where the transalkylation reactor has a liquid hourly space velocity, reducing a temperature of the transalkylation effluent in the C9-effluent heater to produce a cooled transalkylation effluent, where a temperature of the cooled transalkylation effluent between 136 deg C. and 166 deg C., reducing the temperature of the transalkylation effluent in an effluent-transalkylation exchanger to produce a cooled effluent, where a temperature of the cooled effluent is between 83 deg C. and 103 deg C., reducing the temperature of the cooled effluent in a transalkylation cooler to produce a cooled mixed effluent, where a temperature of the cooled mixed effluent is between 35 deg C. and 45 deg C., separating the cooled mixed effluent in a transalkylation separator to produce a separated transalkylation effluent and a light gases stream, increasing a temperature of the separated transalkylation effluent in the effluent-transalkylation exchanger to produce a transalkylation splitter feed, where a temperature of the transalkylation splitter feed is between 105 deg C. and 125 deg C., introducing the transalkylation splitter feed to the splitter unit, where the transalkylation effluent includes light gases, toluene, benzene, mixed xylenes, and C9+ aromatics, separating the transalkylation splitter feed in the splitter unit such that mixed xylenes in the transalkylation splitter feed exit the splitter unit as part of the mixed xylene stream, reducing a temperature of the mixed xylene stream in the feed exchanger to produce a cooled mixed stream, where a temperature of the cooled mixed stream is between 55 deg C. and 65 deg C., and reducing the temperature of the cooled mixed stream in a xylene cooler to produce a mixed xylene product, where a temperature of the mixed xylene product is between 30 deg C. and 50 deg C.

In certain aspects, the feed exchanger is a cross process exchanger, where the feed exchanger is configured to transfer heat from the mixed xylene stream to the heavy reformate feed. In certain aspects, the feed-effluent exchanger is a cross process exchanger, where the feed-effluent exchanger is configured to transfer heat from the dealkylation effluent to the mixed feed. In certain aspects, the effluent-separator exchanger is a cross process exchanger, where the effluent-separator exchanger is configured to transfer heat from the cooled effluent stream to the separated effluent. In certain aspects, the C9-effluent heater is a cross process exchanger, where the C9-effluent heater is configured to transfer heat from the transalkylation effluent to the mixed transalkylation feed. In certain aspects, the effluent-transalkylation exchanger is a cross process exchanger, where the effluent-transalkylation exchanger is configured to transfer heat from the cooled transalkylation effluent to the separated transalkylation effluent. In certain aspects, the dealkylation temperature is between 200 deg C. and 500 deg C., where the dealkylation pressure is between 5 bar and 40 bar, and where the liquid hourly space velocity in the dealkylation reactor is between 1 hr−1 and 10 hr−1. In certain aspects, the transalkylation temperature is between 300 deg C. and 500 deg C., where the transalkylation pressure is between 10 bar and 40 bar, where the liquid hourly space velocity in the transalkylation reactor is between 0.5 hr−1 and 6 hr−1.

In a second aspect, a method for producing mixed xylenes from a heavy reformate feed is provided. The method includes the steps of introducing the heavy reformate feed to a feed exchanger to produce a hot feed stream, where the feed exchanger increases the temperature of the heavy reformate feed, where the heavy reformate includes aromatic hydrocarbons with nine or more carbon atoms (C9+ aromatics), where the hydrogen feed includes hydrogen gas, mixing the hot feed stream and a hydrogen feed to produce a mixed feed, increasing a temperature of the mixed feed in a feed cross exchanger to produce a heated mixed feed, where a temperature of the heated mixed feed is between 65 deg C. and 90 deg C., increasing the temperature of the heated mixed feed in a feed-xylene exchanger to produce a warm mixed feed, where a temperature of warm mixed feed is between 90 deg C. and 150 deg C., increasing the temperature of the warm mixed feed in a feed-effluent exchanger to produce a hot mixed feed, where a temperature of the hot mixed feed is between 324 deg C. and 344 deg C., increasing the temperature of the hot mixed feed in a feed fired heater to produce a hot reactor feed, where a temperature of the hot reactor feed is between 380 deg C. and 400 deg C., introducing the hot reactor feed to a dealkylation reactor, where the dealkylation reactor includes a dealkylation catalyst, reacting the heavy reformate feed with the hydrogen gas in the presence of the dealkylation catalyst in the dealkylation reactor to produce a dealkylation effluent, where the dealkylation reactor is at a dealkylation temperature, where the dealkylation reactor is at a dealkylation pressure, where the dealkylation reactor has a liquid hourly space velocity, reducing a temperature of the dealkylation effluent in the feed-effluent exchanger to produce a cooled effluent stream, where a temperature of the cooled effluent stream is between 115 deg C. and 145 deg C., reducing the temperature of the cooled effluent in an effluent-separator exchanger to produce an effluent stream, where the temperature of the effluent stream is between 80 deg C. and 110 deg C., reducing the temperature of the effluent stream in the feed cross exchanger to produce a warm effluent, where a temperature of the warm effluent is between 65 deg C. and 80 deg C., reducing the temperature of the warm effluent in an effluent cooler to produce a mixed effluent stream, where a temperature of the mixed effluent stream is between 38 deg C. and 47 deg C., separating the mixed effluent stream in an effluent separator to produce a produced hydrogen and a separated effluent, where the produced hydrogen includes hydrogen, increasing a temperature of the separated effluent in the effluent-separator exchanger to produce a dealkylation splitter feed, where a temperature of the dealkylation splitter feed is between 100 deg C. and 130 deg C., introducing the dealkylation splitter feed to a splitter unit, where the dealkylation effluent includes light gases, toluene, benzene, mixed xylenes, and C9+ aromatics, separating the dealkylation effluent into a light gas product, a toluene stream, a benzene stream, a C9 aromatics stream, a C10+ aromatics stream, and a mixed xylene stream in the splitter unit, where the light gas stream includes light hydrocarbons and hydrogen, where the toluene stream includes toluene, where the benzene stream includes benzene, where the mixed xylene stream includes mixed xylenes, where the C9 stream includes C9 aromatics, where the C10+ aromatics stream includes C10+ aromatics, mixing the toluene stream, the C9 aromatics stream, and a hydrogen stream in a mixer to produce a mixed transalkylation feed, increasing a temperature of the mixed transalkylation feed in a C9-effluent heater to produce a hot transalkylation feed, where a temperature of the hot transalkylation feed is between 330 deg C. and 390 deg C., increasing a temperature of the hot transalkylation feed in a transalkylation fired heater to produce a transalkylation feed, where a temperature of the transalkylation feed is between 380 deg C. and 400 deg C., introducing the transalkylation feed to a transalkylation reactor, where the transalkylation reactor includes a transalkylation catalyst, where the hydrogen stream includes hydrogen gas, reacting the toluene stream and the C9 aromatics stream in the presence of the transalkylation catalyst to produce a transalkylation effluent, where the transalkylation reactor is at a transalkylation temperature, where the transalkylation reactor is at a transalkylation pressure, where the transalkylation reactor has a liquid hourly space velocity, reducing a temperature of the transalkylation effluent in the C9-effluent heater to produce a cooled transalkylation effluent, where a temperature of the cooled transalkylation effluent between 136 deg C. and 166 deg C., reducing the temperature of the cooled transalkylation effluent in an effluent-transalkylation exchanger to produce a cooled effluent, where a temperature of the cooled effluent is between 83 deg C. and 103 deg C., reducing the temperature of the cooled effluent in the feed exchanger to produce a mixed effluent, where a temperature of the mixed effluent is between 45 deg C. and 78 deg C., reducing the temperature of the mixed effluent in a transalkylation cooler to produce a cooled mixed effluent, where a temperature of the cooled mixed effluent is between 35 deg C. and 45 deg C., separating the cooled mixed effluent in a transalkylation separator to produce a separated transalkylation effluent and a light gases stream, increasing a temperature of the separated transalkylation effluent in the effluent-transalkylation exchanger to produce a transalkylation splitter feed, where a temperature of the transalkylation splitter feed is between 105 deg C. and 125 deg C., introducing the transalkylation splitter feed to the splitter unit, where the transalkylation effluent includes light gases, toluene, benzene, mixed xylenes, and C9+ aromatics, separating the transalkylation splitter feed in the splitter unit such that mixed xylenes in the transalkylation splitter feed exit the splitter unit as part of the mixed xylene stream, reducing a temperature of the mixed xylene stream in the feed-xylene exchanger to produce a cooled xylene stream, where a temperature of the cooled xylene stream is between 55 deg C. and 65 deg C., and reducing the temperature of the cooled xylene stream in a xylene cooler to produce a mixed xylene product, where a temperature of the mixed xylene product is between 30 deg C. and 50 deg C.

In certain aspects, the feed exchanger is a cross process exchanger, where the feed exchanger is configured to transfer heat from the mixed xylene stream to the heavy reformate feed. In certain aspects, the feed cross exchanger is a cross process exchanger, where the feed cross exchanger is configured to transfer heat from the effluent stream to the mixed feed. In certain aspects, the feed-xylene exchanger is a cross process exchanger, where the feed-xylene exchanger is configured to transfer heat from the mixed xylene stream to the heated mixed feed. In certain aspects, the feed-effluent exchanger is a cross process exchanger, where the feed-effluent exchanger is configured to transfer heat from the dealkylation effluent to the warm mixed feed.

BRIEF DESCRIPTION OF THE DRAWINGS

These and other features, aspects, and advantages of the scope will become better understood with regard to the following descriptions, claims, and accompanying drawings. It is to be noted, however, that the drawings illustrate only several embodiments and are therefore not to be considered limiting of the scope as it can admit to other equally effective embodiments.

Figure 1:
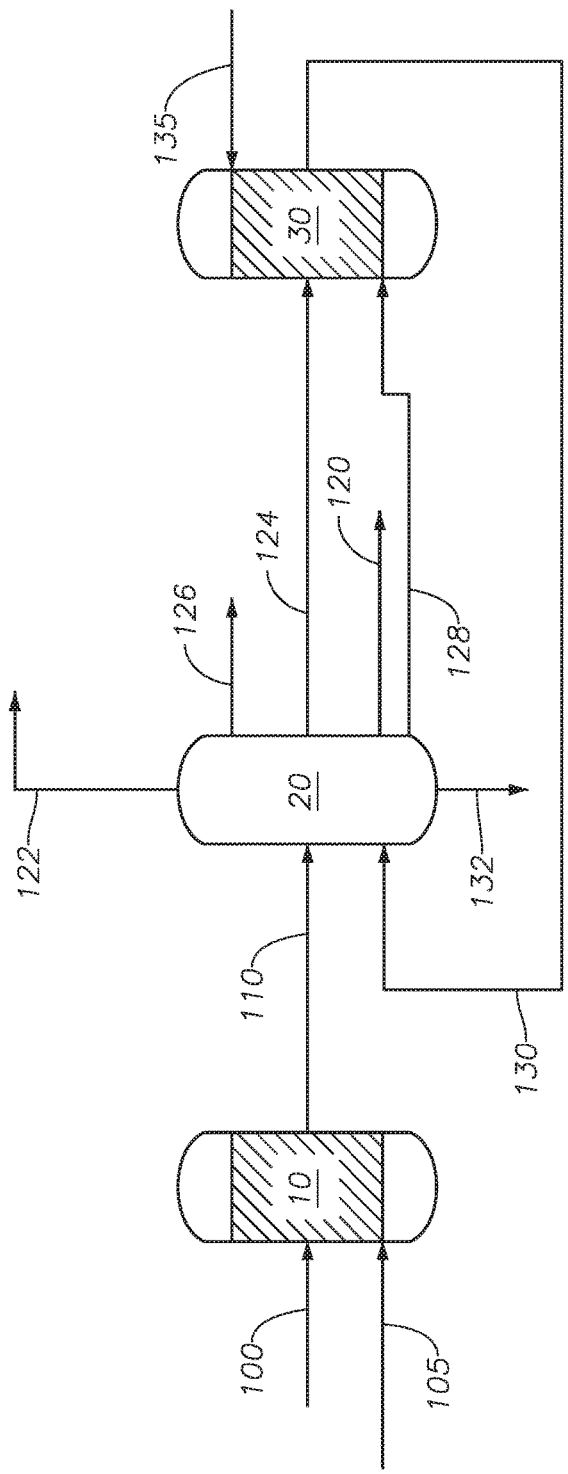
FIG. 1 provides a process diagram of an embodiment of the process.

In the accompanying Figures, similar components or features, or both, may have a similar reference label.

DETAILED DESCRIPTION

While the scope of the apparatus and method will be described with several embodiments, it is understood that one of ordinary skill in the relevant art will appreciate that many examples, variations and alterations to the apparatus and methods described here are within the scope and spirit of the embodiments.

Accordingly, the embodiments described are set forth without any loss of generality, and without imposing limitations, on the embodiments. Those of skill in the art understand that the scope includes all possible combinations and uses of particular features described in the specification.

Described here are processes and systems of a three unit system for the production of mixed xylenes. A heavy reformate is introduced to a dealkylation reactor. The dealkylation effluent from the dealkylation reactor is introduced to a splitter unit to separate the components of the dealkylation effluent. The toluene and C9+ aromatics from the splitter unit are introduced to a transalkylation reactor. Optionally, the benzene can be introduced to the transalkylation reactor also. The transalkylation effluent from the transalkylation reactor is introduced to the splitter unit to separate the components of the transalkylation effluent. The streams exiting the splitter unit include the components of the effluents from both the dealkylation reactor and the transalkylation reactor.

Advantageously, the combination of a dealkylation reactor and a separate transalkylation reactor increases the overall production of xylenes as compared to a one-reactor system that contains both a dealkylation catalyst and a transalkylation catalyst or a single catalyst capable of both dealkylation and transalkylation reactions. Advantageously, recycling the transalkylation effluent to the splitter unit increases overall yield because it minimizes the loss of xylene by reducing the production of benzene through disproportionation of toluene in the transalkylation reactor. Advantageously, energy optimization allows for the production of xylenes with optimized heat integration. There are two primary reactions that occur in the transalkylation reactor to form xylene, an equilibrium transalkylation reaction of toluene and trimethylbenzene and an equilibrium disproportionation reaction of toluene:

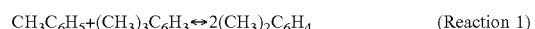
$$CH_3C_6H_5+(CH_3)_3C_6H_3 \leftrightarrow 2(CH_3)_2C_6H_4 \qquad \text{(Reaction 1)}$$

$$2CH_3C_6H_5 \leftrightarrow C_6H_6+(CH_3)_2C_6H_4 \qquad \text{(Reaction 2)}$$

Recycling benzene will limit the production of benzene through Reaction 2, reducing the consumption of toluene in Reaction 2 making more toluene available for the production of xylene in Reaction 1.

As used throughout, a reference to "C" and a number refers to the number of carbon atoms in a hydrocarbon. For example, C1 refers to a hydrocarbon with one carbon atom and C6 refers to a hydrocarbon with six carbon atoms.

As used throughout, "C9 aromatics" refers to aromatic hydrocarbons with nine carbon atoms. Examples of C9 aromatic hydrocarbons include methylethylbenzene, trimethylbenzene, and propylbenzene.

As used throughout, "trimethylbenzene" includes each of the isomers of trimethylbenzene: hemellitene, pseudocumene, and mesitylene.

As used throughout, "C10+ aromatics" refers to aromatic hydrocarbons with ten carbon atoms and aromatics with more than ten carbon atoms, such as an aromatic hydrocarbon with eleven carbon atoms.

As used throughout, "C9+ aromatics" refers to the group of C9 aromatics and C10+ aromatics.

As used throughout, "mixed xylenes" refers to one or more of para-xylene (p-xylene), meta-xylene (m-xylene), and ortho-xylene (o-xylene).

As used throughout, "dealkylation reaction" refers to a reaction that results in the removal of an alkyl group from one or more of the reactants.

As used throughout, "transalkylation reaction" refers to a reaction that results in the transfer of an alkyl group from one or compound to another.

As used throughout, "light hydrocarbons" refers to one or more of alkanes, including methane, ethane, propane, butanes, pentanes, alkenes, and trace amounts of naphthenes, such as cyclopentane, cyclohexane.

As used throughout, "light gases" refers to one or more of light hydrocarbons, hydrogen, and air.

Referring to FIG. 1 an embodiment of the process for producing mixed xylenes in provided. Heavy reformate feed 100 is introduced to dealkylation reactor 10 along with hydrogen feed 105. Heavy reformate feed 100 can include toluene, mixed xylenes, C9 aromatics, and C9+ aromatics. In at least one embodiment, heavy reformate feed 100 can include trace amounts of C8+ naphthenes and C10+ naphthylenes, including the alkyl derivatives of the same. In at least one embodiment, heavy reformate feed 100 can contain between 0 wt % and 10 wt % mixed xylenes and between 60 wt % and 100 wt % C9+ aromatics. In at least one embodiment, heavy reformate feed 100 can contain between 0 wt % and 60 wt % toluene. In at least one embodiment, heavy reformate feed 100 can contain between 0 wt % and 10 wt % mixed xylenes, between 0 wt % and 60 wt % toluene, and between 60 wt % and 100 wt % C9+ aromatics. In at least one embodiment, heavy reformate feed 100 contains between 60 wt % and 100 wt % C9 aromatics and is in the absence of C10+ aromatics.

Hydrogen feed 105 can be any stream containing hydrogen gas. Hydrogen feed 105 can be a stream of pure hydrogen from a fresh hydrogen source. In at least one embodiment described with reference to FIG. 2, hydrogen gas can be recovered from the process in gas separator 40 as produced hydrogen 145, which can be divided such that a portion of produced hydrogen 145 can be recycled as hydrogen feed 105 and introduced to dealkylation reactor 10. In at least one embodiment, hydrogen feed 105 can be from a hydrogen source in a refinery and can contain light hydrocarbons.

Returning to FIG. 1, dealkylation reactor 10 can be any type of reactor capable of containing and supporting a dealkylation reaction. Dealkylation reactor 10 can be a fixed bed reactor or a fluidized bed reactor. The dealkylation temperature in dealkylation reactor 10 can be between 200 degrees Celsius (deg C.) and 500 deg C. The dealkylation pressure in dealkylation reactor 10 can be between 5 bar (500 kilopascal (kPa)) and 40 bar (4000 kPa). The liquid hourly space velocity (LHSV) can be between 1 per hour ($hr^{-1}$) and 10 $hr^{-1}$.

Dealkylation reactor 10 can include a dealkylation catalyst. The dealkylation catalyst can include any catalysts capable of catalyzing dealkylation reactions. Examples of dealkylation catalyst can include bifunctional catalysts such as those described in U.S. Pat. No. 9,000,247. The dealkylation catalyst can be selected to selectively convert one or more of the C9+ aromatics over the others in dealkylation reactions. Dealkylation reactions can convert C9+ aromatics to toluene, benzene, mixed xylenes, and light gases; and can convert C10+ aromatics to C9+ aromatics. Reactions in dealkylation reactor 10 can remove methyl, ethyl, propyl, butyl and pentyl groups, and their isomers, attached to C10+ aromatics. In at least one embodiment, a dealkylation catalyst can be selected to convert more than 97.5 wt % of the methylethylbenzene to toluene. In at least one embodiment, the overall conversion of C9+ aromatics can be above 98 wt % due to conversion of C9 aromatics and the removal of methyl, ethyl, propyl, butyl and pentyl groups attached to C10+ aromatics. Dealkylation effluent 110 can contain mixed xylenes, toluene, benzene, light gases, and C9+ aromatics.

In at least one embodiment, where hydrogen feed 105 is introduced to dealkylation reactor 10, dealkylation reactor 10 is a fixed bed reactor and the light gases produced in dealkylation effluent 110 contain alkanes. In at least one embodiment, dealkylation reactor 10 is in the absence of a hydrogen stream (not shown), dealkylation reactor 10 is a fluidized bed reactor and the light gases produced in dealkylation effluent 110 contain alkenes.

Dealkylation effluent 110 is introduced to splitter unit 20.

Splitter unit 20 can be any type of separation unit capable of separating a stream into its component parts. In at least one embodiment, splitter unit 20 can be one splitter column designed to separate the feed stream into multiple split streams. In at least one embodiment, splitter unit 20 can be multiple splitter columns in series designed to separate one component from the feed stream. In at least one embodiment, splitter unit 20 can be one or more distillation units. In at least one embodiment, where splitter unit 20 is multiple splitter columns, splitter unit 20 includes five splitter columns: a first column operates at a pressure of between 4 bar gauge (barg) and 6 barg and a temperature between 100 deg C. and 200 deg C. to separate light gases from the first column feed to produce light gas stream 122 and a first column effluent; a second column operates at a pressure of between 0.6 barg and 1.5 barg and a temperature between 100 deg C. and 170 deg C. to separate benzene and toluene from the first column effluent to produce a benzene/toluene stream and a second column effluent; a third column operates at a pressure of between 0.3 barg and 0.9 barg and a temperature between 70 deg C. and 150 deg C. to separate benzene from the benzene/toluene stream to produce benzene stream 126 and to separate toluene from the benzene toluene stream to produce toluene stream 124; a fourth column operates at a pressure of between 0.3 barg and 2 barg and a temperature between 120 deg C. and 210 deg C. to separate xylenes from the second column effluent to produce mixed xylene stream 120 and a C9+ aromatics stream; and a fifth column operates at a pressure of between 0.5 barg and 3 barg and a temperature of between 150 deg C. and 250 deg C. to separate C9 aromatics from the C9+ aromatics stream to produce C9 aromatics stream 128 and to separate C10+ aromatics from the C9+ aromatics stream to produce C10+ aromatics stream 132. In at least one embodiment, where splitter unit 20 is multiple splitter columns, splitter unit 20 can be in the absence of a column to separate C9 aromatics from C10+ aromatics, such that the column to separate xylenes produces the xylene stream and a C9+ stream. The C9+ stream can be introduced to the transalkylation reactor. In at least one embodiment, where splitter unit 20 is multiple splitter columns, splitter unit 20 can be in the absence of a column to separate benzene/toluene stream. It can be understood by one of skill in the art that splitter unit 20 can be designed to operate at a temperature and pressure to produce the desired streams. In at least one embodiment, where splitter unit 20 is one distillation column, the distillation column can include multiple sections in one vessel, where each section has the operating conditions corresponding to each of the separate columns described in this paragraph.

Splitter unit 20 separates the components to produce mixed xylene stream 120, light gas stream 122, toluene stream 124, benzene stream 126, C9 aromatics stream 128, and C10+ aromatics stream 132. Mixed xylene stream 120 contains mixed xylenes. Light gas stream 122 contains light gases. Toluene stream 124 contains toluene. Benzene stream 126 contains benzene. C9 aromatics stream 128 contains C9 aromatics, including C9 aromatics formed in dealkylation reactor 10 and unreacted C9 aromatics from heavy reformate feed 100. C10+ aromatics stream 132 contains C10+ aromatics, including C10+ aromatics formed in dealkylation reactor 10 and unreacted C10+ aromatics from heavy reformate feed 100. In at least one embodiment, C10+ aromatics stream 132 can be purged from the system. In at least one embodiment, C10+ aromatics stream 132 can be introduced to dealkylation reactor 10 for further processing to increase the conversion of C10+ aromatics.

Advantageously, the separation and removal of mixed xylenes in the splitter unit increases production of mixed xylenes in the transalkylation reactor. The absence of mixed xylenes in the feed to transalkylation reactor 30 drives the thermodynamic equilibrium of Reaction 1 towards xylene production in transalkylation reactor 30.

Toluene stream 124 and C9 aromatics stream 128 are introduced to transalkylation reactor 30 along with hydrogen stream 135. Hydrogen stream 135 can be any stream containing hydrogen gas. Hydrogen stream 135 can be a stream of pure hydrogen from a fresh hydrogen source. In at least one embodiment described with reference to FIG. 2, produced hydrogen 145 can be divided such that a portion of produced hydrogen 145 can be recycled as hydrogen feed 105 and introduced to dealkylation reactor 10 and a second portion of produced hydrogen can be recycled as hydrogen stream 135 and introduced to transalkylation reactor 30.

Transalkylation reactor 30 can be a fixed bed reactor or a fluidized bed reactor. The transalkylation temperature in transalkylation reactor 30 can be between 300 deg C. and 500 deg C. The transalkylation pressure in transalkylation reactor 30 can be between 10 bar (1000 kPa) and 40 bar (4000 kPa). The liquid hourly space velocity (LHSV) can be between 0.5 hr$^{-1}$ and 6 hr$^{-1}$. The operating conditions can be set to maximize the production of xylenes. The temperature can have a greater influence on the transalkylation reaction than pressure. It is understood that higher temperatures, higher pressures, and lower LHSV favor transalkylation reactions, while higher temperatures can lead to catalyst deactivation and therefore, the operating conditions must be balanced to maximize production and minimize catalyst deactivation.

Transalkylation reactor 30 can include a transalkylation catalyst. The transalkylation catalyst can include any catalyst capable of catalyzing transalkylation reactions. Examples of transalkylation catalysts include bifunctional catalysts as described in U.S. Pat. No. 9,000,247. The transalkylation catalyst can be selected to selectively convert one or more of the C9+ aromatics over the others in transalkylation reactions. In at least one embodiment, the transalkylation catalyst can be selected to selectively convert trimethylbenzenes to mixed xylenes. Transalkylation reactions can occur to convert C9+ aromatics to toluene, benzene, mixed xylenes, and light gases. Transalkylation effluent 130 contains mixed xylenes, toluene, benzene, light gases, and C9+ aromatics.

Figure 3:
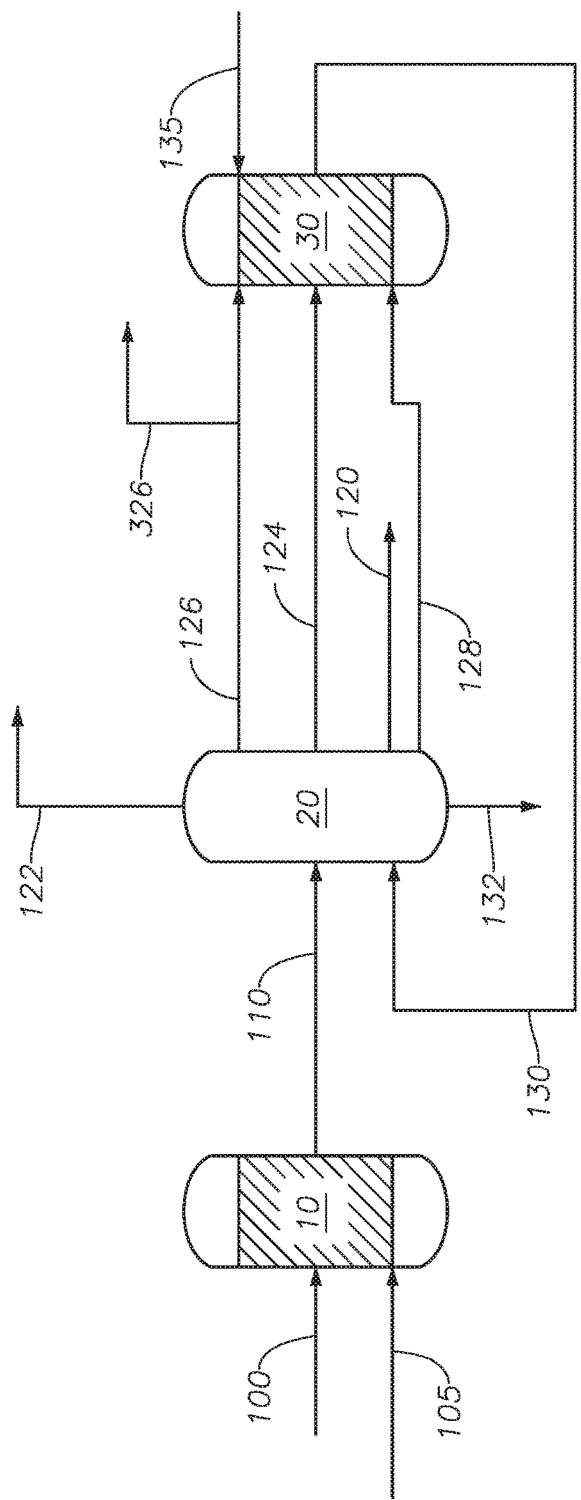
FIG. 3 provides a process diagram of an embodiment of the process.

In at least one embodiment, with reference to FIG. 3, benzene stream 126 can be introduced to transalkylation reactor 30. In at least one embodiment, a slip stream can be removed from benzene stream 126 as benzene product 326. The volume of benzene stream 126 introduced to transalkylation reactor 30 can be determined based on the reaction conditions desired in transalkylation reactor 30. In at least one embodiment, the volume of benzene stream 126 introduced to transalkylation reactor 30 can be controlled by the flow rate of benzene product 326. Adding benzene from benzene stream 126 to transalkylation reactor 30 can minimize the production of benzene through Reaction 2 and increase the production of mixed xylenes through Reaction 1.

Transalkylation reactor 30 produces transalkylation effluent 130. Transalkylation effluent 130 can contain mixed xylenes, toluene, benzene, light gases, and C9+ aromatics, including C9+ aromatics formed in transalkylation reactor 30 and unreacted C9+ aromatics from heavy reformate feed 100.

Transalkylation effluent 130 can be introduced to splitter unit 20. Transalkylation effluent 130 is separated in splitter unit 20 and the component parts form part of mixed xylene stream 120, light gas stream 122, toluene stream 124, benzene stream 126, C9 aromatics stream 128, and C10+ aromatics stream 132.

The overall yield of mixed xylenes in mixed xylene stream 120 can be between 30 wt % and 89 wt %. In at least one embodiment, the overall yield of mixed xylenes in mixed xylene stream 120 is 80 wt %. The overall yield of toluene can be between 0 wt % and 20 wt % and alternately between 5 wt % and 20 wt %. The overall yield of benzene can be between 0 wt % and 10 wt % and alternately between 1 wt % and 10 wt %. Mixed xylene stream 120 can be introduced to an isomerization unit or a crystallization unit to convert m-xylene and o-xylene to p-xylene.

Figure 2:
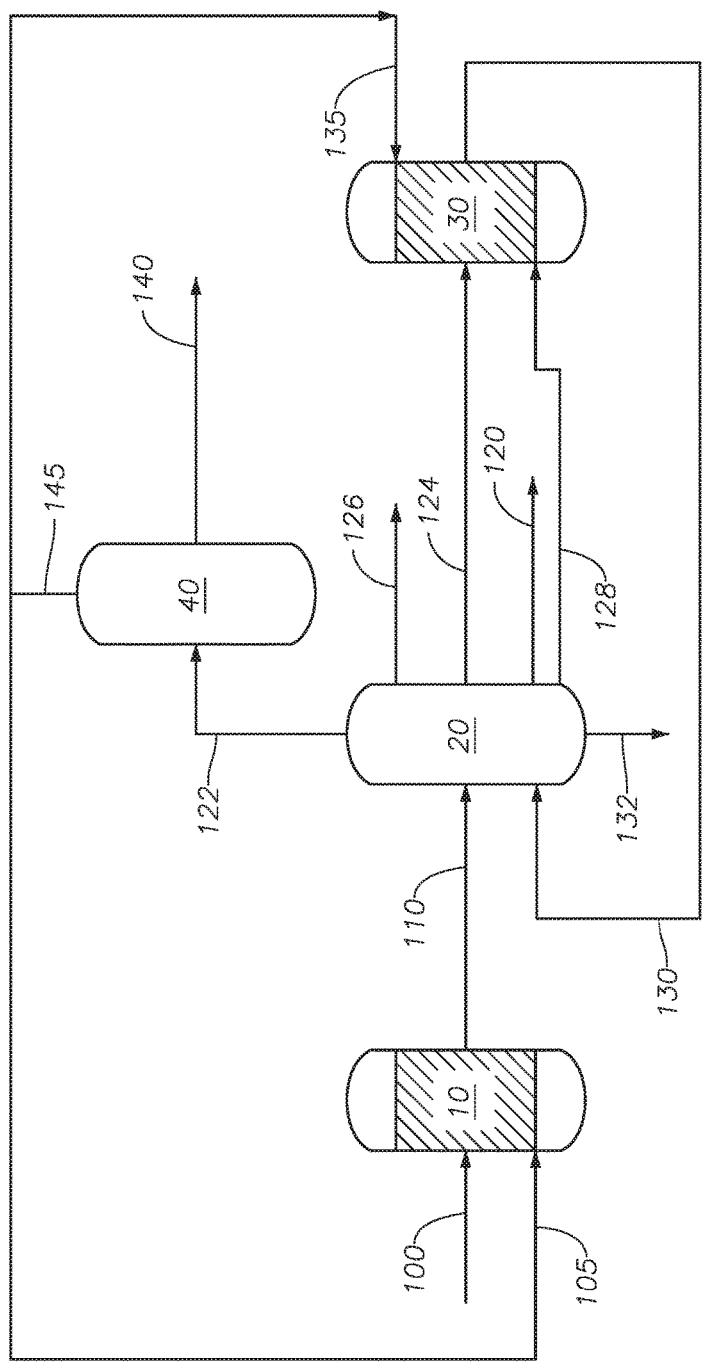
FIG. 2 provides a process diagram of an embodiment of the process.

Referring to FIG. 2, an embodiment of the process to produce mixed xylenes is provided. Light gas stream 122 is introduced to gas separator 40. Gas separator 40 can be any type of separation unit capable of separating hydrogen from a stream of gases. In at least one embodiment, gas separator 40 is a pressure swing adsorption unit. In at least one embodiment, gas separator 40 is a hydrogen membrane separation unit. Gas separator 40 can separate light gas stream 122 into light gas product 140 and produced hydrogen 145. Produced hydrogen 145 can be split to create hydrogen feed 105 and hydrogen stream 135. Light gas product 140 contains light hydrocarbons. Produced hydrogen 145 contains hydrogen. Light gas product 140 can be purged to the atmosphere, used as a source fuel, or sent for further processing.

Figure 4:
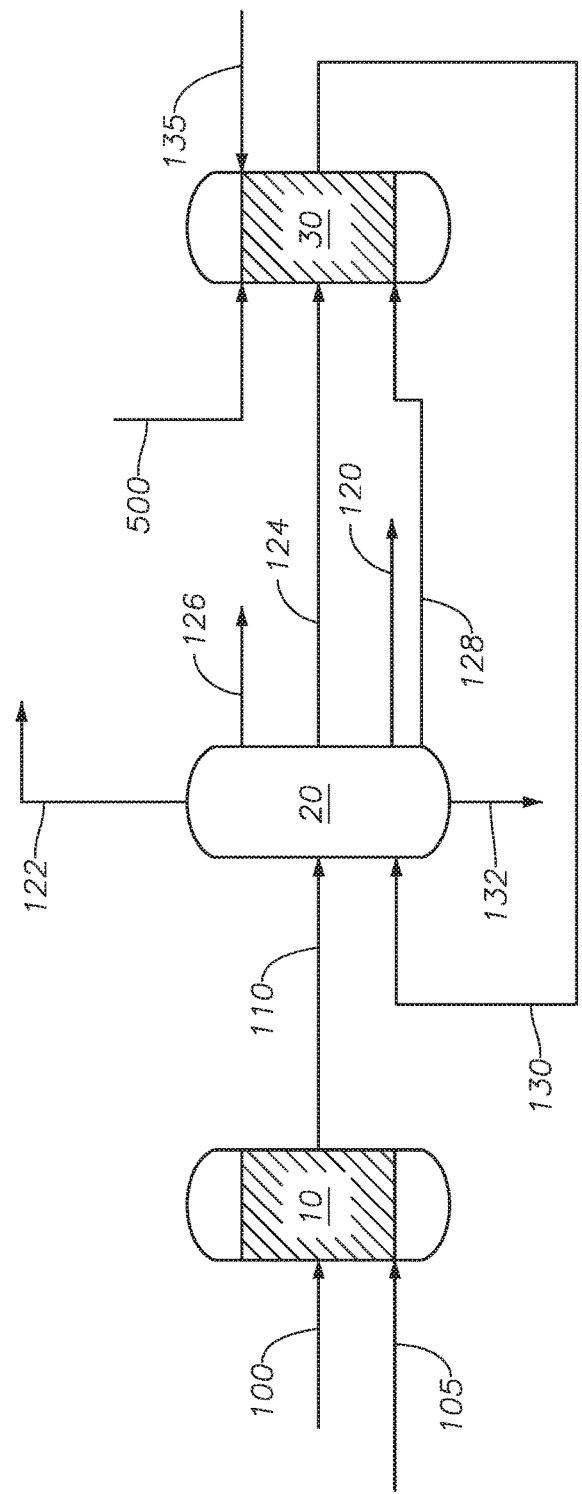
FIG. 4 provides a process diagram of an embodiment of the process.

Referring to FIG. 4, an embodiment of the process to produce mixed xylenes is provided with reference to FIG. 1. Added aromatic stream 500 is introduced to transalkylation reactor 30. Added aromatic stream 500 can include toluene, benzene, or combinations of the same. In at least one embodiment, added aromatic stream 500 includes toluene. The flow rate of added aromatic stream 500 can be at a volume to provide surplus toluene to increase conversion of trimethylbenzene in the reaction between toluene and trimethylbenzene present in C9 aromatics stream 128. Added aromatic stream 500 can be used to increase the methyl group to aromatic ratio to 2, which can increase the conversion of C9 aromatics to xylenes. In at least one embodiment, dealkylation reactor 10 is in the absence of an added aromatic stream.

In at least one embodiment, the dealkylation reactor and the transalkylation reactor can be housed in one vessel, where the two reactor stages are physically separate from each other with no mingling of the internal gases. The effluent from the dealkylation reactor stage can exit the vessel and enter a splitter unit where the benzene stream, toluene stream, and C9 aromatics stream can be separated and then reintroduced to the vessel in the transalkylation reactor stage.

Advantageously, the position of the dealkylation reactor upstream of the transalkylation produces toluene not present in the heavy reformate feed, toluene is a reactant in transalkylation reactions to produce xylene, thus a process with the dealkylation reactor upstream of the transalkylation increases xylene production. Advantageously, the position of the dealkylation reactor upstream of the transalkylation reactor reduces the amount of C9 aromatics and C10+ aromatics being introduced to the transalkylation reactor.

Both the dealkylation reactor and the transalkylation reactor are in the absence of methanol and in the absence of methylation reactions, which are irreversible reactions that add a methyl group to a compound. In at least one embodiment, the heavy reformate feed is in the absence of ethylbenzene.

Figure 10:
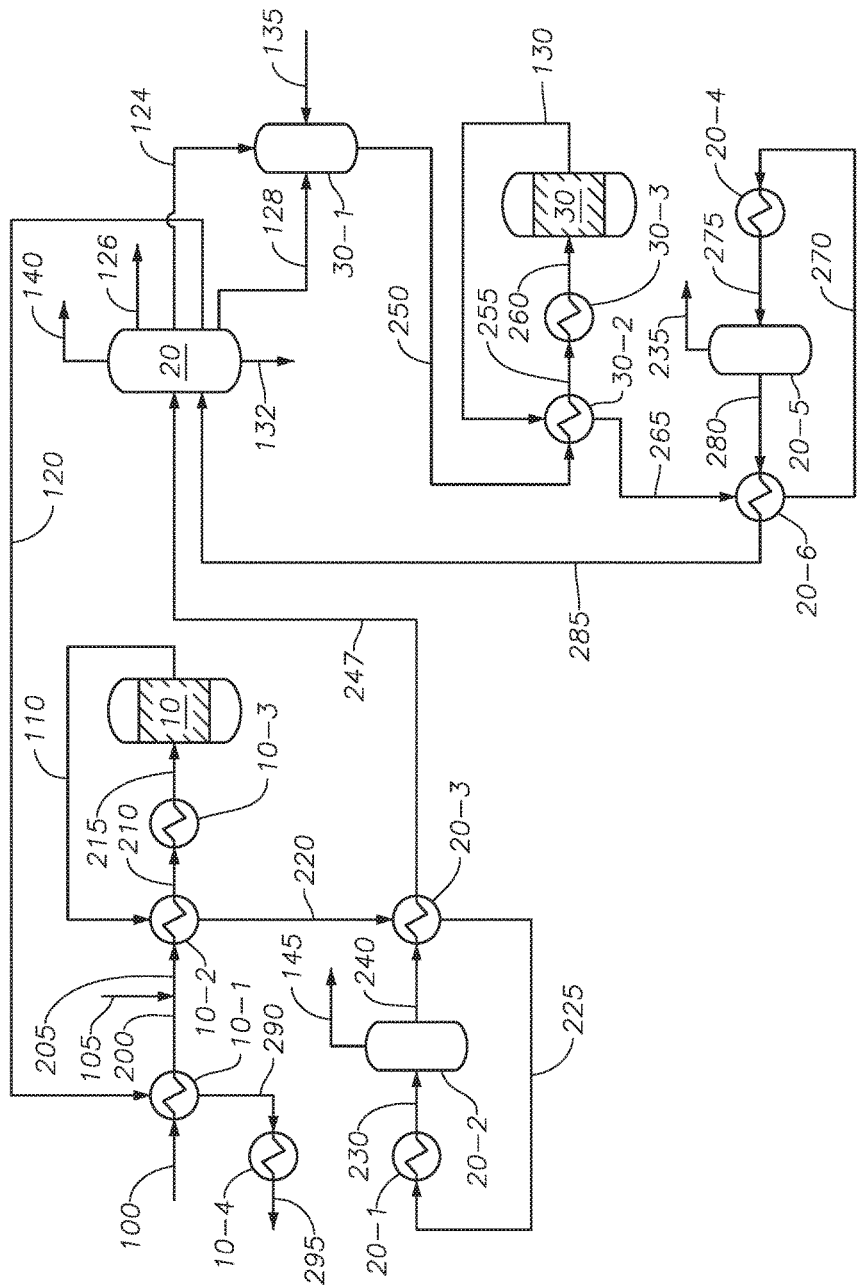
FIG. 10 provides a process diagram of an embodiment of the process with energy optimization.
Figure 11:
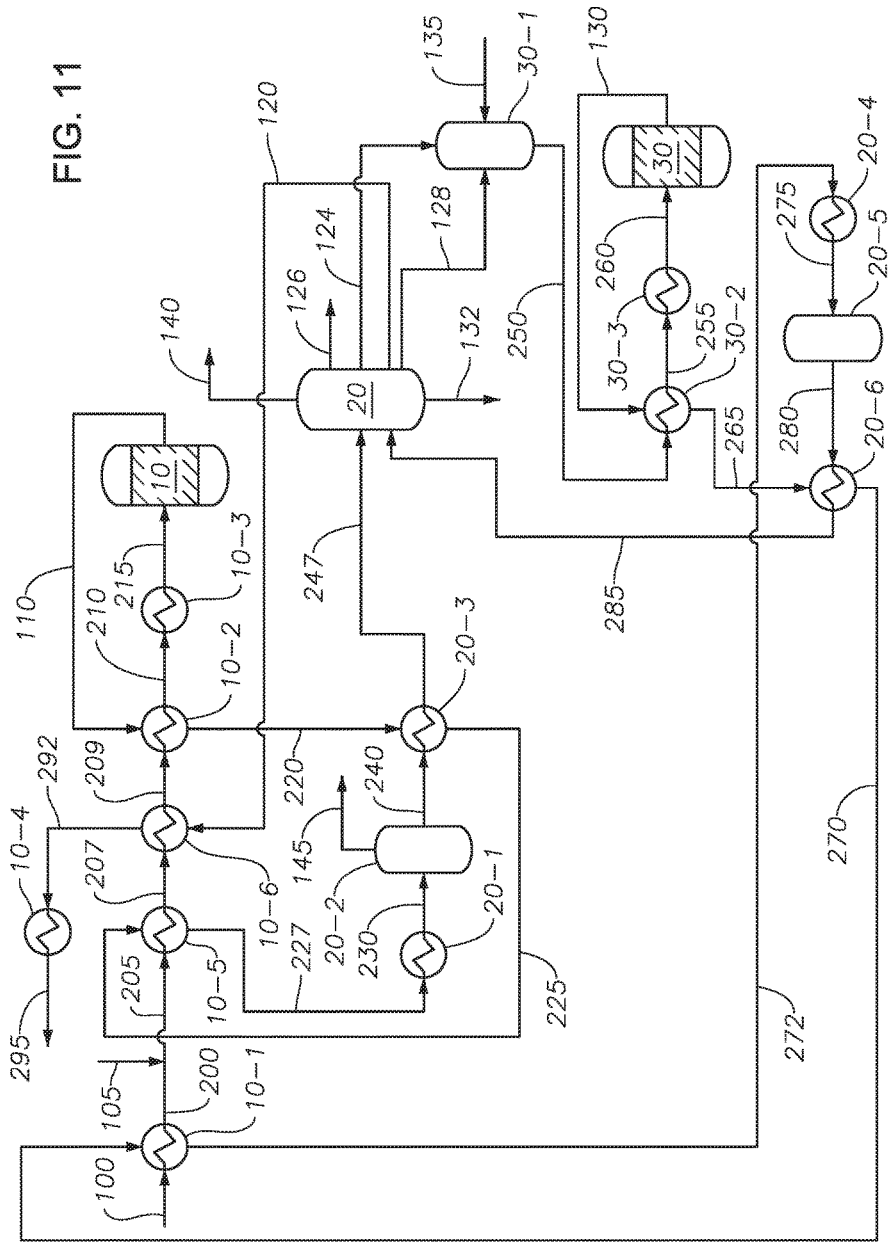
FIG. 11 provides a process diagram of an embodiment of the process with energy optimization.

Heat exchangers and separators can be included in the process to produce mixed xylenes. Advantageously, cross-exchangers can be used to optimize energy consumption across the entire system and process. An embodiment of energy optimization of the process to produce mixed xylenes is described with reference to FIG. 10. The energy optimization of the process to produce mixed xylenes incorporates cross process exchangers, which can be any type of heat exchanger capable of transferring heat from one process stream to a separate process stream. The cross process exchangers can include parallel-flow exchangers, counter-flow exchangers, and cross-flow exchangers. Examples of cross process exchangers can include shell and tube heat exchangers, plate heat exchangers, spiral heat exchangers, and combinations of the same. Referring to FIG. 10, feed exchanger 10-1, feed-effluent exchanger 10-2, effluent-separator exchanger 20-3, C9-effluent heater 30-2, and effluent-transalkylation exchanger 20-6 are cross process exchangers. Referring to FIG. 11, feed cross exchanger 10-5 feed-xylene exchanger 10-6 are cross process exchangers. Advantageously, maximizing the number of cross process exchangers reduces the energy input required for the system and optimizes the overall energy consumption. Other sources of heat can include fired heaters, which can be any type of direct heat exchanger. Referring to FIG. 10, feed fired heater 10-3 and transalkylation fired heater 30-3 can be fired heaters. Other units to remove heat from process streams can include heat exchangers, which can be any type of heat exchanger where a non-process stream fluid medium is used to remove heat from a process stream. Examples of heat exchangers can include shell and tube heat exchangers, plate heat exchangers, spiral heat exchangers, and combinations of the same. Referring to FIG. 10, xylene cooler 10-4, effluent cooler 20-1, and transalkylation cooler 20-4 are heat exchangers where the heat is removed using a non-process stream fluid medium.

Heavy reformate 100 can be heated in feed exchanger 10-1 to produce hot feed stream 200. The temperature of hot feed stream 200 can be between 105 deg C. and 125 deg C. Hot feed stream 200 and hydrogen feed 105 can be mixed to produce mixed feed 205. Mixed feed 205 can be heated in feed-effluent exchanger 10-2 to produce hot mixed feed 210. Hot mixed feed 210 can have a temperature between 324 deg C. and 344 deg C. Hot mixed feed 210 can be heated in feed fired heater 10-3 to produce hot reactor feed 215. Hot reactor feed 215 can be at a temperature between 380 deg C. and 400 deg C. Hot reactor feed 215 can be reacted in dealkylation reactor 10 to produce dealkylation effluent 110. Dealkylation effluent 110 can be at a temperature between 350 deg C. and 420 deg C. Dealkylation effluent 110 can be cooled in feed-effluent exchanger 10-2 to produce cooled effluent stream 220. Cooled effluent stream 220 can be at a temperature between 115 deg C. and 145 deg C.

Cooled effluent stream 220 can be cooled in effluent-separator exchanger 20-3 to produce effluent stream 225. Effluent stream 225 can be at a temperature between 80 deg C. and 110 deg C. Effluent stream 225 can be cooled in effluent cooler 20-1 to produced mixed effluent stream 230. Mixed effluent stream 230 can be at a temperature between 38 deg C. and 47 deg C. Hydrogen in mixed effluent stream 230 can be separated in effluent separator 20-2 to produce produced hydrogen 145 and separated effluent 240. Separated effluent 240 can be heated in effluent-separator exchanger 20-3 to produce dealkylation splitter feed 247. Dealkylation splitter feed 247 can be at a temperature in the range of 100 deg C. and 130 deg C.

Dealkylation splitter feed 247 can be separated in splitter unit 20 to produce light gas product 140, toluene stream 124, benzene stream 126, C9 aromatics stream 128, C10+ aromatics stream 132, and mixed xylene stream 120. Toluene stream 124, C9 aromatics stream 128, and hydrogen stream 135 can be mixed in mixer 30-1 to produce mixed transalkylation feed 250. Mixed transalkylation feed 250 can be heated in C9-effluent heater 30-2 to produce hot transalkylation feed 255. Hot transalkylation feed 255 can be at a temperature between 330 deg C. and 390 deg C. Hot transalkylation feed 255 can be heated in transalkylation fired heater 30-3 to produce transalkylation feed 260. Transalkylation feed 260 can be at a temperature between 380 deg C. and 400 deg C.

Transalkylation feed 260 can be reacted in transalkylation reactor 30 to produce transalkylation effluent 130. Transalkylation effluent 130 can be cooled in transalkylation cooler 20-4 to produce cooled transalkylation effluent 265. Cooled transalkylation effluent 265 can be at a temperature between 136 deg C. and 166 deg C. Cooled transalkylation effluent 265 can be cooled in effluent-transalkylation exchanger 20-6 to produce cooled effluent 270. Cooled effluent 270 can be at a temperature between 83 deg C. and 103 deg C. Cooled effluent 270 can be cooled in transalkylation cooler 20-4 to produce cooled mixed effluent 275. Cooled mixed effluent 275 can be at a temperature between 35 deg C. and 45 deg C. Light gases stream 235 can be separated in transalkylation separator 20-5 to produce separated transalkylation effluent 280. Light gases stream 235 can include light gases. Separated transalkylation effluent 280 can be heated in effluent-transalkylation exchanger 20-6 to produce transalkylation splitter feed 285. Transalkylation splitter feed 285 can be at a temperature between 105 deg C. and 125 deg C.

Mixed xylene stream 120 can be cooled in feed exchanger 10-1 to produce cooled mixed stream 290. Cooled mixed stream 290 can be at a temperature between 55 deg C. and 65 deg C. Cooled mixed stream 290 can be cooled in xylene cooler 10-4 to produce mixed xylene product 295. The temperature of mixed xylene product 295 can be between 30 deg C. and 50 deg C.

Referring to FIG. 11, an alternate embodiment of the energy optimization of the process to produce mixed xylenes is described and can be understood with reference to FIG. 10. Additional cross process exchangers are included. Mixed feed 205 can be heated in feed cross exchanger 10-5 to produce heated mixed feed 207. Heated mixed feed 207 can be at a temperature between 65 deg C. and 90 deg C. Heated mixed feed 207 can be heated in feed-xylene exchanger 10-6 to produce warm mixed feed 209. Warm mixed feed 209 can be at a temperature between 90 deg C. and 150 deg C. Warm mixed feed 209 can be heated in feed-effluent exchanger 10-2 to produce hot mixed feed 210.

Effluent stream 225 can be cooled in feed cross exchanger 10-5 to produce warm effluent 227. The temperature of warm effluent 227 can be in the range between 65 deg C. and 80 deg C. Warm effluent 227 can be cooled in effluent cooler 20-1 to produce mixed effluent stream 230.

Cooled effluent 270 can be cooled in feed exchanger 10-1 to produce mixed effluent 272. The temperature of mixed effluent 272 can be in the range between 45 deg C. and 78 deg C. Mixed effluent 272 can be cooled in transalkylation cooler 20-4 to produce cooled mixed effluent 275. Mixed xylenes 120 can be cooled in feed-xylene exchanger 10-6 to produce cooled xylene stream 292. Cooled xylene stream 292 can be at a temperature between 80 deg C. and 100 deg C. Cooled xylene stream 292 can be cooled in xylene cooler 10-4 to produce mixed xylene product 295.

EXAMPLES

The following examples were carried out in laboratory equipment.

Example 1

Example 1 provides an analysis of dealkylation reactor 10 with reference to FIG. 2. Heavy reformate feed 100 had the composition in Table 1. Hydrogen feed 105 was recycled from produced hydrogen 145 after being recovered from gas separator 40.

TABLE 1

Composition of heavy reformate feed 100

| Component | Composition, wt % |
|---|---|
| Ethylbenzene | 0.0498 |
| Mixed xylenes | 5.1789 |
| C9 aromatics total | 80.1502 |
| Trimethylbenzene | 56.5475 |
| Methylethylbenzene | 21.0869 |
| Propylbenzene | 2.5158 |
| C10+ aromatics | 14.6211 |

Dealkylation reactor 10 was at a temperature of 400 deg C. and a pressure of 30 bar (3000 kPa). The weight hourly space velocity (whsv) was 4.2 per hour ($hr^{-1}$). The ratio of hydrogen gas ($H_2$) to hydrocarbons was 4:1 (mol/mol). The catalyst was a ZSM-5 catalyst designed for dealkylation reactions to selectively convert methylethylbenzenes to toluene, benzene, and light alkanes. The composition of dealkylation effluent 110 is shown in Table 2.

TABLE 2

Composition of dealkylation effluent 110

| Component | Composition, wt % |
|---|---|
| Light hydrocarbons | 7.00 |
| Benzene | 2.49 |
| Toluene | 16.26 |
| Ethylbenzene | 0.04 |
| Mixed xylenes | 16.49 |
| C9 aromatics total | 50.65 |
| Trimethylbenzene | 50.39 |
| Methylethylbenzene | 0.26 |
| Propylbenzene | 0 |
| C10+ aromatics | 7.08 |

The conversion of methylethylbenzene in dealkylation reactor 10 was 98.8 wt %. The conversion of trimethylbenzene in dealkylation reactor 10 was 10.9 wt %.

Example 2

Example 2 provides an analysis of transalkylation reactor 30 with reference to FIG. 2. The combined feed to transalkylation reactor 30 had the composition in Table 3.

TABLE 3

Composition of feed to transalkylation reactor 30

| Component | Composition, wt % |
|---|---|
| Toluene | 50 |
| Trimethylbenzene | 50 |

Transalkylation reactor 30 was at a temperature of 400 deg C. and a pressure of 30 bar (3000 kPa). The whsv was 4.2 $hr^{-1}$. The ratio of hydrogen gas ($H_2$) to hydrocarbons is 4:1 (mol/mol). The catalyst was a transalkylation catalyst with a zeolite. The composition of transalkylation effluent 130 is shown in Table 4.

TABLE 4

Composition of transalkylation effluent 130

| Component | Composition, wt % |
|---|---|
| Light hydrocarbons | 8.4 |
| Benzene | 3.9 |
| Toluene | 22.1 |
| Ethylbenzene | 0.3 |
| Mixed xylenes | 37 |
| C9 aromatics total | 20.8 |
| Trimethylbenzene | 19.9 |
| Methylethylbenzene | 0.9 |
| Propylbenzene | 0 |
| C10+ aromatics | 6.3 |

The conversion of trimethylbenzene in transalkylation reactor 30 was 56 wt %. The conversion of toluene in transalkylation reactor 30 was 52 wt %.

Example 3

Figure 5:
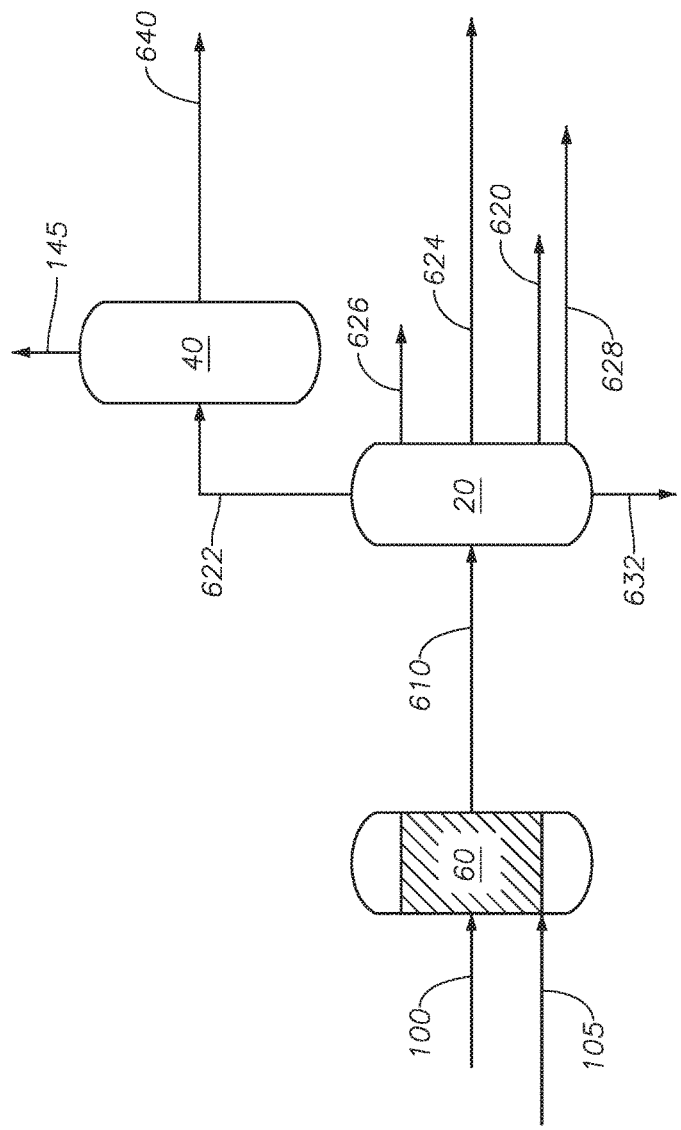
FIG. 5 provides a process diagram of a one-reactor system.

Example 3 was a comparative example of a one-reactor system, where dealkylation reactions and transalkylation reactions occur in the same reactor, coupled with a splitter unit described with reference to FIG. 5 and FIG. 2. Heavy reformate feed 100, having the composition described in Table 5, was introduced to transalkylation-dealkylation reactor 60 along with hydrogen feed 105. Hydrogen feed 105 was simulated as a feed from a hydrogen source in a refinery containing only hydrogen.

TABLE 5

Composition of heavy reformate feed 100

| Component | Composition, kilogram per hour (kg/hr) | | |
|---|---|---|---|
| | Heavy Reformate Feed 100 | Hydrogen Feed 105 | Produced Hydrogen 145 |
| Hydrogen | 0 | 20 | 16.5 |
| Light hydrocarbons | 0 | 0 | 0 |
| Benzene | 0 | 0 | 0 |
| Toluene | 0 | 0 | 0 |
| Ethylbenzene | 0 | 0 | 0 |
| Mixed xylenes | 51 | 0 | 0 |
| C9 aromatics total | 835 | 0 | 0 |
| Trimethylbenzene | 592 | — | — |
| Methylethylbenzene | 213 | — | — |
| Propylbenzene | 30 | — | — |
| C10+ aromatics | 114 | 0 | 0 |

Transalkylation-dealkylation reactor 60 was operated at a temperature of 400 deg C., a pressure of 20 bar, a whsv of 4.2 hr$^{-1}$, and a hydrogen to hydrocarbon ratio of 4:1. The catalyst was a catalyst was a 40% beta and 60% MCM-41 catalyst that can facilitate both transalkylation and dealkylation reactions.

One-reactor effluent 610 was introduced to splitter unit 20. Splitter unit 20 operated to separate one-reactor effluent 610 into its component parts, as shown in Table 6. Light product 622 was introduced to gas separator 40 which separated hydrogen from light hydrocarbons to produce produced hydrogen 145 and gas product 640 containing light hydrocarbons.

TABLE 6

Composition of Streams Exiting Splitter Unit 20 in Example 3

| Component | Composition, kg/hr | | | | | |
|---|---|---|---|---|---|---|
| | Light gas 622 | Benzene 626 | Toluene 624 | Xylene 620 | C9 Aromatics 628 | C10+ Aromatics 632 |
| Hydrogen | 16.5 | 0 | 0 | 0 | 0 | 0 |
| Light hydrocarbons | 20.6 | 0 | 0 | 0 | 0 | 0 |
| Benzene | 0 | 12.0 | 0 | 0 | 0 | 0 |
| Toluene | 0 | 0 | 113.6 | 0 | 0 | 0 |
| Ethylbenzene | 0 | 0 | 0 | 3.6 | 0 | 0 |
| Mixed xylenes | 0 | 0 | 0 | 339.7 | 0 | 0 |
| C9 aromatics total | 0 | 0 | 0 | 0 | 366.7 | 0 |
| Trimethylbenzene | — | — | — | — | 324.9 | — |
| Methylethylbenzene | — | — | — | — | 41.7 | — |
| Propylbenzene | — | — | — | — | 0 | — |
| C10+ aromatics | 0 | 0 | 0 | 0 | 0 | 147.3 |

The mixed xylene yield was 34 wt %, which was in the range of xylene yield for a one-reactor system, of between 32 wt % and 35 wt %. In a one-reactor system, the production of xylene is limited by the thermodynamic equilibrium, as shown in Reaction 1. The conversion of methylethylbenzene was 80%, which falls within then typical range of methylethylbenzene conversion in a one-reactor system of between 80 wt % and 92 wt %. The conversion of trimethylbenzene was 45%, which was slightly outside of the typical range of trimethylbenzene conversion of around 50 wt %.

Example 4

Figure 6:
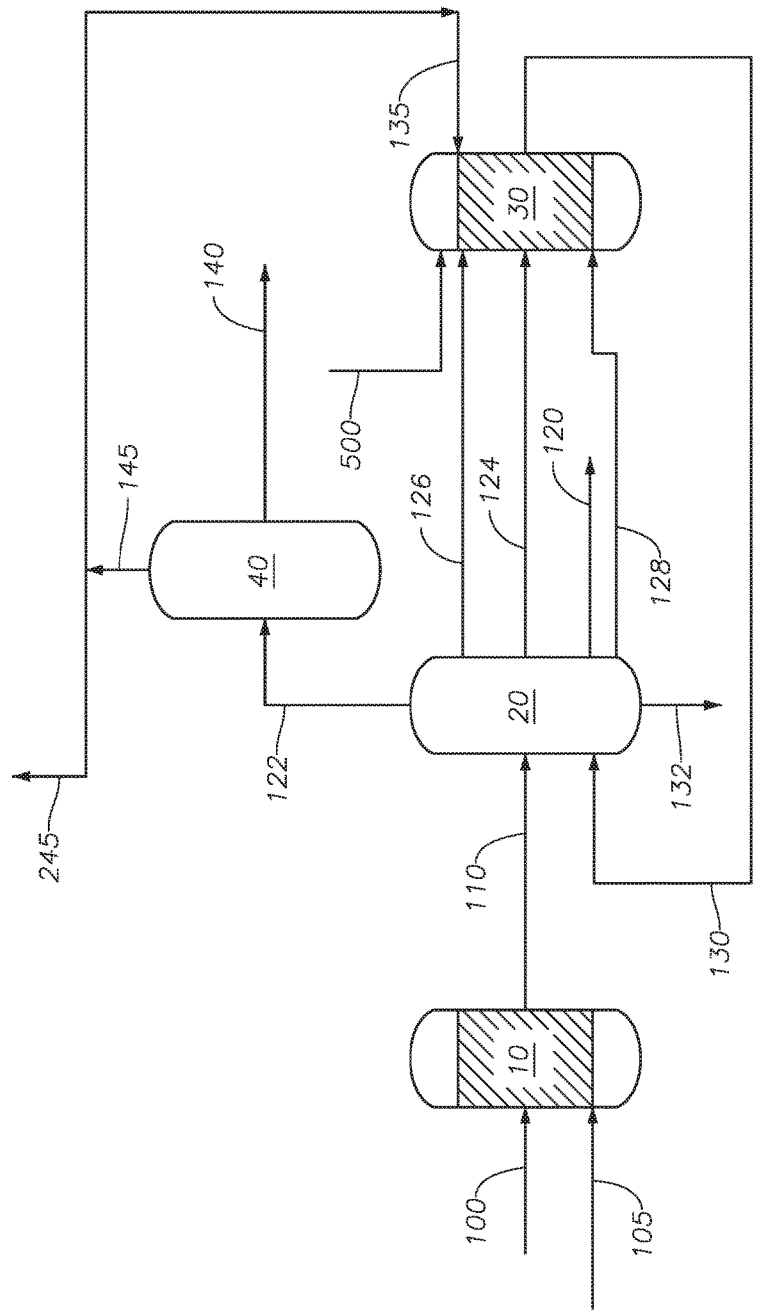
FIG. 6 provides a process diagram of an embodiment of the process.

Example 4 was a simulation of the process to produce mixed xylenes with reference to FIG. 6 and FIG. 2. Heavy reformate feed 100, having the composition in Table 7, is introduced to dealkylation reactor 10 along with hydrogen feed 105. The flow rate of hydrogen feed 105 was 138.6 kg/hr, with 66.5 kg/hr of hydrogen gas and 72.0 kg/hr light hydrocarbons.

TABLE 7

Composition of heavy reformate feed 100

| Component | Composition, kg/hr | Composition, wt % |
|---|---|---|
| Mass Flow | 1000.0 | 100 |
| Hydrogen | 0 | 0.0 |
| Light gases | 0 | 0.0 |
| Benzene | 0 | 0.0 |
| Toluene | 0 | 0.0 |
| Ethylbenzene | 0.5 | 0.0 |
| Mixed xylenes | 51.8 | 5.2 |
| m-xylene | 31.8 | 3.2 |
| o-xylene | 10.0 | 1.0 |
| p-xylene | 10.0 | 1.0 |
| C9 aromatics total | 801.6 | 80.2 |
| Trimethylbenzene | 565.5 | 56.5 |
| Methylethylbenzene | 210.9 | 21.1 |
| Propylbenzene | 25.2 | 2.5 |
| C10+ aromatics | 146.2 | 14.6 |

Dealkylation reactor 10 was at a temperature of 400 deg C. and a pressure of 30 bar (3000 kPa). The whsv was 4.2 h$^{-1}$. The ratio of hydrogen gas (H$_2$) to hydrocarbons was 4:1 (mol/mol). The catalyst was a 3-dimensional zeolite-based dealkylation catalyst. The composition of dealkylation effluent 110 is shown in Table 8.

TABLE 8

Composition of dealkylation effluent 110

| Component | Composition, kg/hr | Composition, wt % without hydrogen gas |
|---|---|---|
| Mass Flow | 1138.6 | — |
| Hydrogen | 63.0 | — |
| Light gases | 106.5 | 9.9 |
| Benzene | 26.8 | 2.5 |

TABLE 8-continued

Composition of dealkylation effluent 110

| Component | Composition, kg/hr | Composition, wt % without hydrogen gas |
|---|---|---|
| Toluene | 174.9 | 16.3 |
| Ethylbenzene | 0.4 | 0.0 |
| Mixed xylenes | 177.5 | 16.5 |
| m-xylene | 102.2 | 9.5 |
| o-xylene | 39.9 | 3.7 |
| p-xylene | 35.4 | 3.3 |
| C9 aromatics total | 506.4 | 47.1 |
| Trimethylbenzene | 503.8 | 46.8 |
| Methylethylbenzene | 2.5 | 0.2 |
| Propylbenzene | 0.0 | 0.0 |
| C10+aromatics | 83.1 | 7.7 |

Dealkylation effluent 110 was introduced to splitter unit 20 which separated dealkylation effluent 110 into its component parts. Light gas stream 122 was introduced to gas separator 40 to produce light gas product 140 and produced hydrogen 145. Produced hydrogen 145 was split to produce hydrogen slipstream 245 and hydrogen stream 135. The composition and flow rates are shown in Table 9.

TABLE 9

Composition of streams

| | Composition, kg/hr | | | | |
|---|---|---|---|---|---|
| Component | Stream 122 | Stream 140 | Stream 145 | Stream 135 | Stream 245 |
| Mass Flow | 407.6 | 222.1 | 185.5 | 126.9 | 58.6 |
| Hydrogen | 185.5 | 0.0 | 185.5 | 126.9 | 58.6 |
| Light gases | 222.1 | 222.1 | 0.0 | 0.0 | 0.0 |
| Benzene | 0.0 | 0.0 | 0.0 | 0.0 | 0.0 |
| Toluene | 0.0 | 0.0 | 0.0 | 0.0 | 0.0 |
| Ethylbenzene | 0.0 | 0.0 | 0.0 | 0.0 | 0.0 |
| Mixed xylenes | 0.0 | 0.0 | 0.0 | 0.0 | 0.0 |
| m-xylene | — | — | — | — | — |
| o-xylene | — | — | — | — | — |
| p-xylene | — | — | — | — | — |
| C9 aromatics total | 0.0 | 0.0 | 0.0 | 0.0 | 0.0 |
| Trimethylbenzene | — | — | — | — | — |
| Methylethylbenzene | — | — | — | — | — |
| Propylbenzene | — | — | — | — | — |
| C10+ aromatics | 0.0 | 0.0 | 0.0 | 0.0 | 0.0 |

Benzene stream 126, toluene stream 124, and C9 aromatics stream 128 were introduced to transalkylation reactor 30 along with added aromatic stream 500 and hydrogen stream 135. The flow rate of added aromatic stream 500 was 70.0 kg/hr of pure toluene which creates a surplus of toluene in transalkylation reactor 30. Transalkylation reactor 30 was at a temperature of 400 deg C. and a pressure of 30 bar (3000 kPa). The whsv was 4.2 $h^{-1}$. The ratio of hydrogen gas ($H_2$) to hydrocarbons is 4:1 (mol/mol). The catalyst was a 1-dimensional zeolite-based transalkylation catalyst. The transalkylation catalyst was not the same as the dealkylation catalyst. The composition of various streams are shown in Table 10.

TABLE 10

Composition of Streams

| | Composition, kg/hr (wt % calculated with no hydrogen gas) | | | | | |
|---|---|---|---|---|---|---|
| Component | Stream 120 | Stream 124 | Stream 126 | Stream 128 | Stream 132 | Stream 130 |
| Mass Flow | 844.8 | 537.4 | 62.8 | 1003.2 | 83.1 | 1800.3 |
| Hydrogen | 0.0 | 0.0 | 0.0 | 0.0 | 0.0 | 122.4 |
| Light hydrocarbons | 0.0 | 0.0 | 0.0 | 0.0 | 0.0 | 115.6 |
| Benzene | 0.0 | 0.0 | 62.8 (100) | 0.0 | 0.0 | 36.1 (6.9) |
| Toluene | 0.0 | 537.4 (100) | 0.0 | 0.0 | 0.0 | 362.5 (21.6) |
| Ethylbenzene | 30.3 (3.6) | 0.0 | 0.0 | 0.0 | 0.0 | 29.9 (1.8) |
| Mixed xylenes | 814.5 (96.4) | 0.0 | 0.0 | 0.0 | 0.0 | 637.1 (38.0) |
| m-xylene | 469.0 (55.5) | — | — | — | — | 366.8 (21.9) |
| o-xylene | 183.1 (21.7) | — | — | — | — | 143.2 (8.5) |
| p-xylene | 162.4 (19.2) | — | — | — | — | 127.0 (7.6) |
| C9 aromatics total | 0.0 | 0.0 | 0.0 | 1003.2 (100) | 0.0 | 496.8 (29.6) |
| Trimethylbenzene | — | — | — | 998.7 (99.5) | — | 494.8 (29.5) |
| Methylethylbenzene | — | — | — | 4.5 (0.5) | — | 2.0 (0.1) |
| Propylbenzene | — | — | — | 0.0 (0.0) | — | 0.0 |
| C10 + aromatics | 0.0 | 0.0 | 0.0 | 0.0 | 83.1 (100) | 0.0 |

The production of mixed xylenes in Example 4 was 814.5 kg/hr. The overall conversion of trimethylbenzene and methylethylbenzene was 100%.

Example 5

Figure 7:
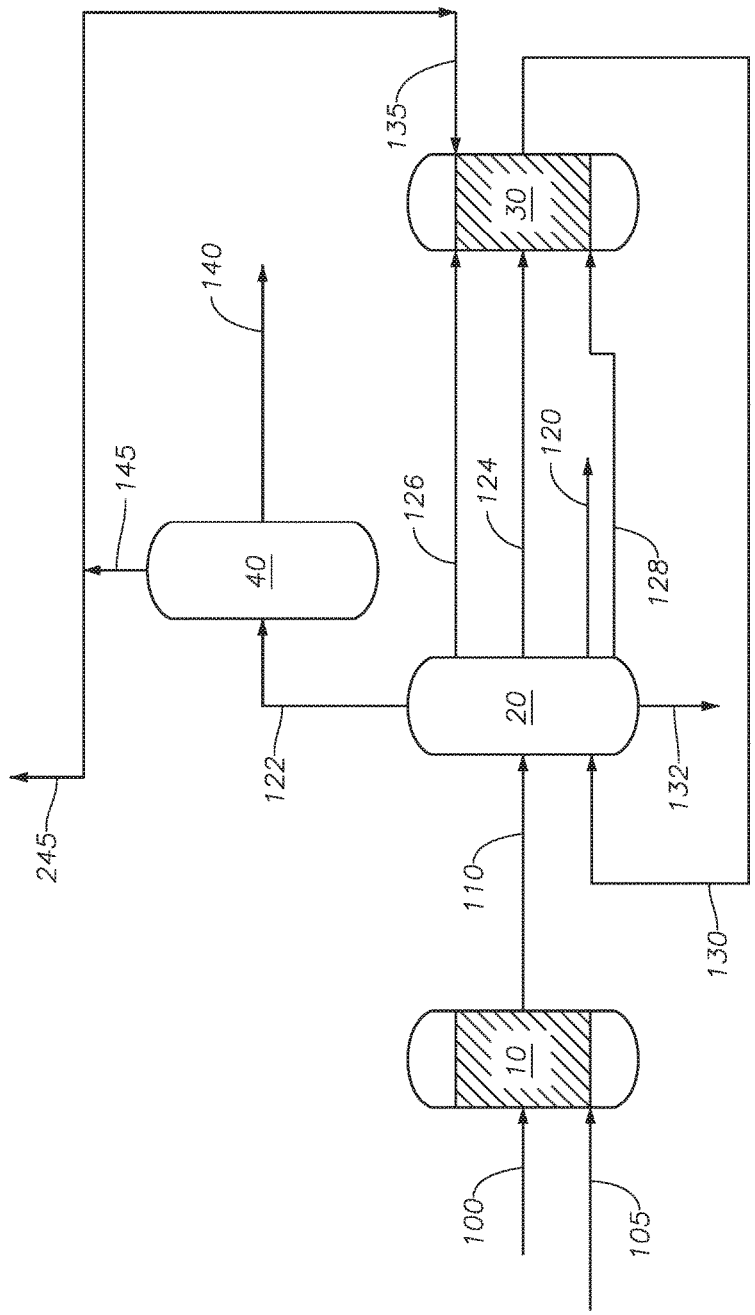
FIG. 7 provides a process diagram of an embodiment of the process.

Example 5 was a simulation of the process to produce mixed xylenes with reference to FIG. 7. Heavy reformate feed 100, having the composition in Table 11, was introduced to dealkylation reactor 10 along with hydrogen feed 105. The flow rate of hydrogen feed 105 was 138.6 kg/hr with 66.5 kg/hr hydrogen gas and 72.0 kg/hr light hydrocarbons.

TABLE 11

Composition of heavy reformate feed 100

| Component | Composition, kg/hr | Composition, wt % |
|---|---|---|
| Mass Flow | 1000.0 | 100 |
| Hydrogen | 0 | 0.0 |
| Light gases | 0 | 0.0 |

TABLE 11-continued

Composition of heavy reformate feed 100

| Component | Composition, kg/hr | Composition, wt % |
|---|---|---|
| Benzene | 0 | 0.0 |
| Toluene | 0 | 0.0 |
| Ethylbenzene | 0.5 | 0.0 |
| Mixed xylenes | 51.8 | 5.2 |
| m-xylene | 31.8 | 3.2 |
| o-xylene | 10.0 | 1.0 |
| p-xylene | 10.0 | 1.0 |
| C9 aromatics total | 801.6 | 80.2 |
| Trimethylbenzene | 565.5 | 56.5 |
| Methylethylbenzene | 210.9 | 21.1 |
| Propylbenzene | 25.2 | 2.5 |
| C10+ aromatics | 146.2 | 14.6 |

Dealkylation reactor 10 was at a temperature of 400 deg C. and a pressure of 30 bar (3000 kPa). The whsv was 4.2 $hr^{-1}$. The ratio of hydrogen gas ($H_2$) to hydrocarbons was 4:1 (mol/mol). The catalyst was a 3-dimensional zeolite-based dealkylation catalyst. The composition of dealkylation effluent 110 is shown in Table 12.

TABLE 12

Composition of dealkylation effluent 110

| Component | Composition, kg/hr | Composition, wt % calculated without hydrogen gas |
|---|---|---|
| Mass Flow | 1138.6 | — |
| Hydrogen | 63.0 | — |
| Light gases | 106.5 | 9.9 |
| Benzene | 26.8 | 2.5 |
| Toluene | 174.9 | 16.3 |
| Ethylbenzene | 0.4 | 0.0 |
| Mixed xylenes | 177.5 | 16.5 |
| m-xylene | 102.2 | 9.5 |
| o-xylene | 39.9 | 3.7 |
| p-xylene | 35.4 | 3.3 |
| C9 aromatics total | 506.4 | 47.1 |
| Trimethylbenzene | 503.8 | 46.8 |
| Methylethylbenzene | 2.5 | 0.2 |
| Propylbenzene | 0.0 | 0.0 |
| C10+ aromatics | 83.1 | 7.7 |

Dealkylation effluent 110 was introduced to splitter unit 20 which separated dealkylation effluent 110 into its component parts. Light gas stream 122 was introduced to gas separator 40 to produce light gas product 140 and produced hydrogen 145. Produced hydrogen 145 was split to produce hydrogen slipstream 245 and hydrogen stream 135. The composition and flow rates are shown in Table 13.

TABLE 13

Composition of streams

| | Composition, kg/hr | | | | |
|---|---|---|---|---|---|
| Component | Stream 122 | Stream 140 | Stream 145 | Stream 135 | Stream 245 |
| Mass Flow | 388.0 | 216.0 | 172.0 | 113.6 | 58.4 |
| Hydrogen | 172.0 | 0.0 | 172.0 | 113.6 | 58.4 |
| Light gases | 216.0 | 216.0 | 0.0 | 0.0 | 0.0 |
| Benzene | 0.0 | 0.0 | 0.0 | 0.0 | 0.0 |
| Toluene | 0.0 | 0.0 | 0.0 | 0.0 | 0.0 |
| Ethylbenzene | 0.0 | 0.0 | 0.0 | 0.0 | 0.0 |
| Mixed xylenes | 0.0 | 0.0 | 0.0 | 0.0 | 0.0 |
| m-xylene | — | — | — | — | — |
| o-xylene | — | — | — | — | — |
| p-xylene | — | — | — | — | — |
| C9 aromatics total | 0.0 | 0.0 | 0.0 | 0.0 | 0.0 |
| Trimethylbenzene | — | — | — | — | — |
| Methylethylbenzene | — | — | — | — | — |
| Propylbenzene | — | — | — | — | — |
| C10+ aromatics | 0.0 | 0.0 | 0.0 | 0.0 | 0.0 |

Benzene stream 126, toluene stream 124, and C9 aromatics stream 128 were introduced to transalkylation reactor 30 with no surplus toluene. Hydrogen stream 135 was introduced to transalkylation reactor 30. Transalkylation reactor 30 was at a temperature of 400 deg C. and a pressure of 30 bar (3000 kPa). The whsv was 4.2 $h^{-1}$. The ratio of hydrogen gas ($H_2$) to hydrocarbons is 4:1 (mol/mol). The catalyst was a 1-dimensional zeolite-based transalkylation catalyst. The transalkylation catalyst was not the same as the dealkylation catalyst. The composition of various streams are shown in Table 14.

TABLE 14

Composition of Streams

Composition, kg/hr (wt % calculated with no hydrogen gas)

| Component | Stream 120 | Stream 124 | Stream 126 | Stream 128 | Stream 132 | Stream 130 |
|---|---|---|---|---|---|---|
| Mass Flow | 781.1 | 452.5 | 49.7 | 1026.2 | 83.1 | 1642.0 |
| Hydrogen | 0.0 | 0.0 | 0.0 | 0.0 | 0.0 | 109.0 |
| Light hydrocarbons | 0.0 | 0.0 | 0.0 | 0.0 | 0.0 | 109.4 (7.1) |
| Benzene | 0.0 | 0.0 | 49.7 (100) | 0.0 | 0.0 | 23.0 (1.5) |
| Toluene | 0.0 | 452.5 (100) | 0.0 | 0.0 | 0.0 | 277.6 (18.1) |
| Ethylbenzene | 25.4 (3.3) | 0.0 | 0.0 | 0.0 | 0.0 | 25.0 (1.6) |
| Mixed xylenes | 755.7 (96.7) | 0.0 | 0.0 | 0.0 | 0.0 | 578.2 (37.7) |
| m-xylene | 435.1 (55.7) | — | — | — | — | 332.9 (21.7) |
| o-xylene | 169.9 (21.8) | — | — | — | — | 130.0 (8.5) |
| p-xylene | 150.7 (19.3) | — | — | — | — | 115.3 (7.5) |
| C9 aromatics total | 0.0 | 0.0 | 0.0 | 1026.2 (100.0) | 0.0 | 519.8 (33.9) |
| Trimethylbenzene | — | — | — | 1021.7 (99.6) | — | 517.8 (33.8) |

TABLE 14-continued

Composition of Streams

Composition, kg/hr (wt % calculated with no hydrogen gas)

| Component | Stream 120 | Stream 124 | Stream 126 | Stream 128 | Stream 132 | Stream 130 |
|---|---|---|---|---|---|---|
| Methylethylbenzene | — | — | — | 4.5 (0.4) | — | 2.0 (0.1) |
| Propylbenzene | — | — | — | 0.0 | — | 0.0 |
| C10+ aromatics | 0.0 | 0.0 | 0.0 | 70.8 | 83.1 (100) | 0.0 (0) |

The production of mixed xylenes in Example 5 was 755.7 kg/hr. The conversion of trimethylbenzene in transalkylation reactor 30 was 51 wt %. The overall conversion of trimethylbenzene from heavy reformate feed 100 to mixed xylene stream 120 is 100 wt %. In other words, all trimethylbenzene in heavy reformate feed 100 is converted to xylenes in mixed xylene stream 120.

Comparing the production of mixed xylenes in Example 4 and Example 5 shows the increased yield due to the addition of surplus toluene to transalkylation reactor 30.

Example 6

Figure 8:
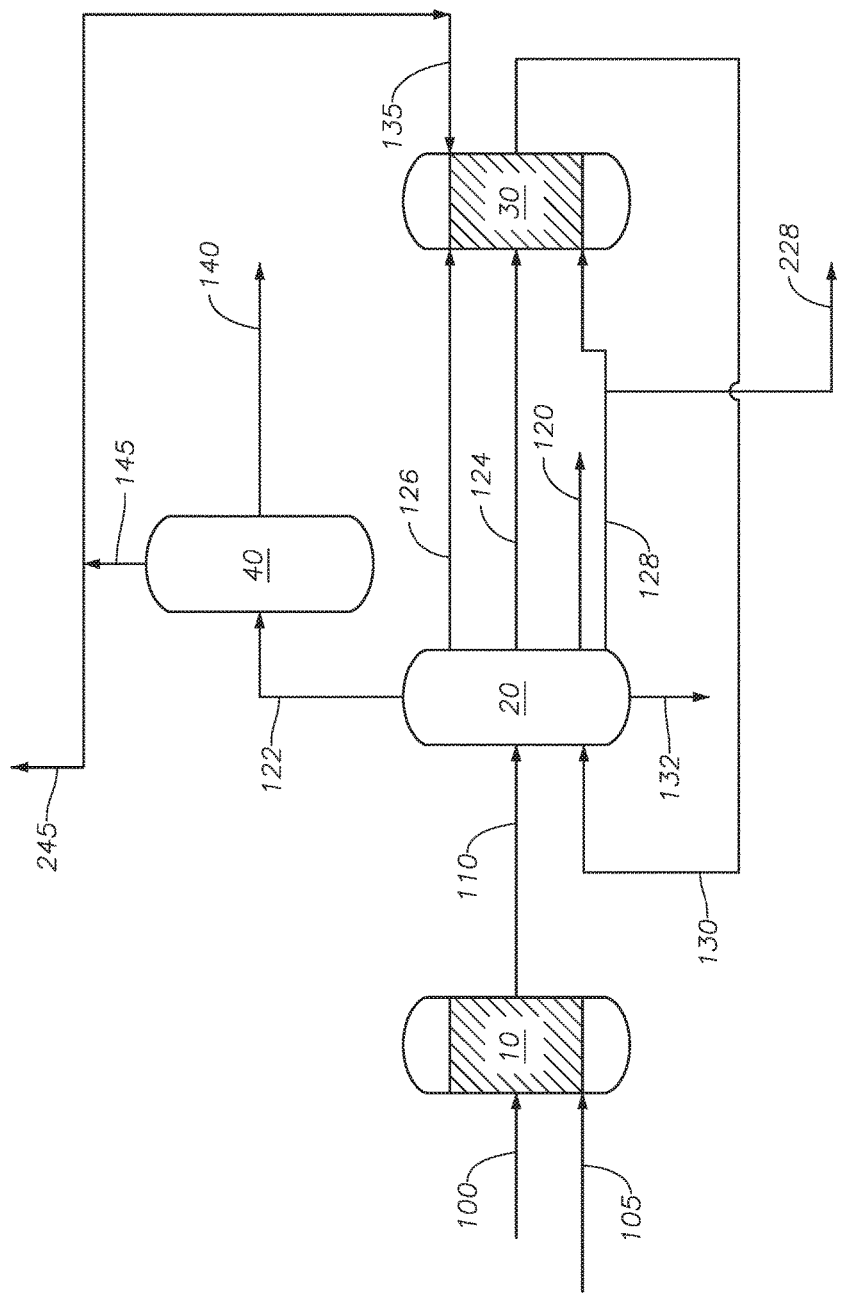
FIG. 8 provides a process diagram of an embodiment of the process.

Example 6 was a simulation of the process to produce mixed xylenes with reference to FIG. 8. Heavy reformate feed 100, having the composition in Table 15, was introduced to dealkylation reactor 10 along with hydrogen feed 105. The flow rate of hydrogen feed 105 was 138.6 kg/hr with 66.5 kg/hr hydrogen gas and 72.0 kg/hr light hydrocarbons.

TABLE 15

Composition of heavy reformate feed 100

| Component | Composition, kg/hr | Composition, wt % |
|---|---|---|
| Mass Flow | 1000.0 | 100 |
| Hydrogen | 0 | 0.0 |
| Light gases | 0 | 0.0 |
| Benzene | 0 | 0.0 |
| Toluene | 0 | 0.0 |
| Ethylbenzene | 0.5 | 0.0 |
| Mixed xylenes | 51.8 | 5.2 |
| m-xylene | 31.8 | 3.2 |
| o-xylene | 10.0 | 1.0 |
| p-xylene | 10.0 | 1.0 |
| C9 aromatics total | 801.6 | 80.2 |
| Trimethylbenzene | 565.5 | 56.5 |
| Methylethylbenzene | 210.9 | 21.1 |
| Propylbenzene | 25.2 | 2.5 |
| C10+ aromatics | 146.2 | 14.6 |

Dealkylation reactor 10 was at a temperature of 400 deg C. and a pressure of 30 bar (3000 kPa). The whsv was 4.2 hr$^{-1}$. The ratio of hydrogen gas (H$_2$) to hydrocarbons was 4:1 (mol/mol). The catalyst was a 3-dimensional zeolite-based dealkylation catalyst. The composition of dealkylation effluent 110 is shown in Table 16.

TABLE 16

Composition of dealkylation effluent 110

| Component | Composition, kg/hr | Composition, wt % calculated without hydrogen gas |
|---|---|---|
| Mass Flow | 1138.6 | — |
| Hydrogen | 63.0 | — |
| Light gases | 106.5 | 9.9 |
| Benzene | 26.8 | 2.5 |
| Toluene | 174.9 | 16.3 |
| Ethylbenzene | 0.4 | 0.0 |
| Mixed xylenes | 177.5 | 16.5 |
| m-xylene | 102.2 | 9.5 |
| o-xylene | 39.9 | 3.7 |
| p-xylene | 35.4 | 3.3 |
| C9 aromatics total | 506.4 | 47.1 |
| Trimethylbenzene | 503.8 | 46.8 |
| Methylethylbenzene | 2.5 | 0.2 |
| Propylbenzene | 0.0 | 0.0 |
| C10+ aromatics | 83.1 | 7.7 |

Dealkylation effluent 110 was introduced to splitter unit 20 which separated dealkylation effluent 110 into its component parts. Light gas stream 122 was introduced to gas separator 40 to produce light gas product 140 and produced hydrogen 145. Produced hydrogen 145 was split to produce hydrogen slipstream 245 and hydrogen stream 135. The composition and flow rates are shown in Table 17.

TABLE 17

Composition of streams

Composition, kg/hr

| Component | Stream 122 | Stream 140 | Stream 145 | Stream 135 | Stream 245 |
|---|---|---|---|---|---|
| Mass Flow | 361.7 | 207.7 | 154.0 | 94.3 | 59.7 |
| Hydrogen | 154.0 | 0.0 | 154.0 | 94.3 | 59.7 |
| Light gases | 207.7 | 207.7 | 0.0 | 0.0 | 0.0 |
| Benzene | 0.0 | 0.0 | 0.0 | 0.0 | 0.0 |
| Toluene | 0.0 | 0.0 | 0.0 | 0.0 | 0.0 |
| Ethylbenzene | 0.0 | 0.0 | 0.0 | 0.0 | 0.0 |
| Mixed xylenes | 0.0 | 0.0 | 0.0 | 0.0 | 0.0 |
| m-xylene | — | — | — | — | — |
| o-xylene | — | — | — | — | — |
| p-xylene | — | — | — | — | — |
| C9 aromatics total | 0.0 | 0.0 | 0.0 | 0.0 | 0.0 |
| Trimethylbenzene | — | — | — | — | — |
| Methylethylbenzene | — | — | — | — | — |
| Propylbenzene | — | — | — | — | — |
| C10+ aromatics | 0.0 | 0.0 | 0.0 | 0.0 | 0.0 |

Benzene stream 126 and toluene stream 124 were introduced to transalkylation reactor 30 with no surplus toluene. Hydrogen stream 135 was introduced to transalkylation reactor 30. C9 aromatics slip stream 228 was separated from C9 aromatics stream 128 with the remaining flow of C9 aromatics stream 128 introduced to transalkylation reactor 30. C9 aromatics slip stream 228 was adjusted to maintain a methyl to aromatic ring ratio of 2 in transalkylation reactor 30 in the absence of an added aromatic stream. Transalkylation reactor 30 was at a temperature of 400 deg C. and a pressure of 30 bar (3000 kPa). The whsv was 4.2 $h^{-1}$. The ratio of hydrogen gas ($H_2$) to hydrocarbons is 4:1 (mol/mol). The catalyst was a 1-dimensional zeolite-based transalkylation catalyst. The transalkylation catalyst was not the same as the dealkylation catalyst. The composition of various streams are shown in Table 18.

TABLE 18

Composition of Streams

Composition, kg/hr (wt % calculated with no hydrogen gas)

| Component | Stream 120 | Stream 124 | Stream 126 | Stream 128 | Stream 228 | Stream 132 | Stream 130 |
|---|---|---|---|---|---|---|---|
| Mass Flow | 672.9 | 444.0 | 53.6 | 859.7 | 115.2 | 83.1 | 1336.3 |
| Hydrogen | 0.0 | 0.0 | 0.0 | 0.0 | 0.0 | 0.0 | 91.0 |
| Light hydrocarbons | 0.0 | 0.0 | 0.0 | 0.0 | 0.0 | 0.0 | 101.2 (8.1) |
| Benzene | 0.0 | 0.0 | 53.6 (100) | 0.0 | 0.0 | 0.0 | 26.8 (2.2) |
| Toluene | 0.0 | 444.0 (100) | 0.0 | 0.0 | 0.0 | 0.0 | 269.1 (21.6) |
| Ethylbenzene | 22.6 (3.4) | 0.0 | 0.0 | 0.0 | 0.0 | 0.0 | 22.2 (1.8) |
| Mixed xylenes | 650.3 (96.6) | 0.0 | 0.0 | 0.0 | 0.0 | 0.0 | 472.8 (38.0) |
| m-xylene | 374.4 (55.6) | — | — | — | — | — | 272.2 (21.9) |
| o-xylene | 146.2 (21.7) | — | — | — | — | — | 106.3 (8.5) |
| p-xylene | 129.7 (19.3) | — | — | — | — | — | 94.3 (7.6) |
| C9 aromatics total | 0.0 | 0.0 | 0.0 | 859.7 (100.0) | 115.2 (100.0) | 0.0 | 353.3 (28.4) |
| Trimethylbenzene | — | — | — | 855.6 (99.5) | 114.7 (99.6) | — | 351.8 (28.2) |
| Methylethylbenzene | — | — | — | 4.1 (0.5) | 0.5 (0.4) | — | 1.6 (0.1) |
| Propylbenzene | — | — | — | 0.0 | 0.0 | — | 0.0 |
| C10+ aromatics | 0.0 | 0.0 | 0.0 | 70.8 | 0.0 | 83.1 (100) | 0.0 (0) |

The production of mixed xylenes in Example 6 was 650.3 kg/hr. The overall conversion of trimethylbenzene is 80 wt %.

Comparing the production rate of mixed xylenes in Example 5 and Example 6 shows that introducing the entire flow rate of the C9 aromatics stream into the transalkylation reactor increases production of mixed xylenes.

Example 7

Figure 9:
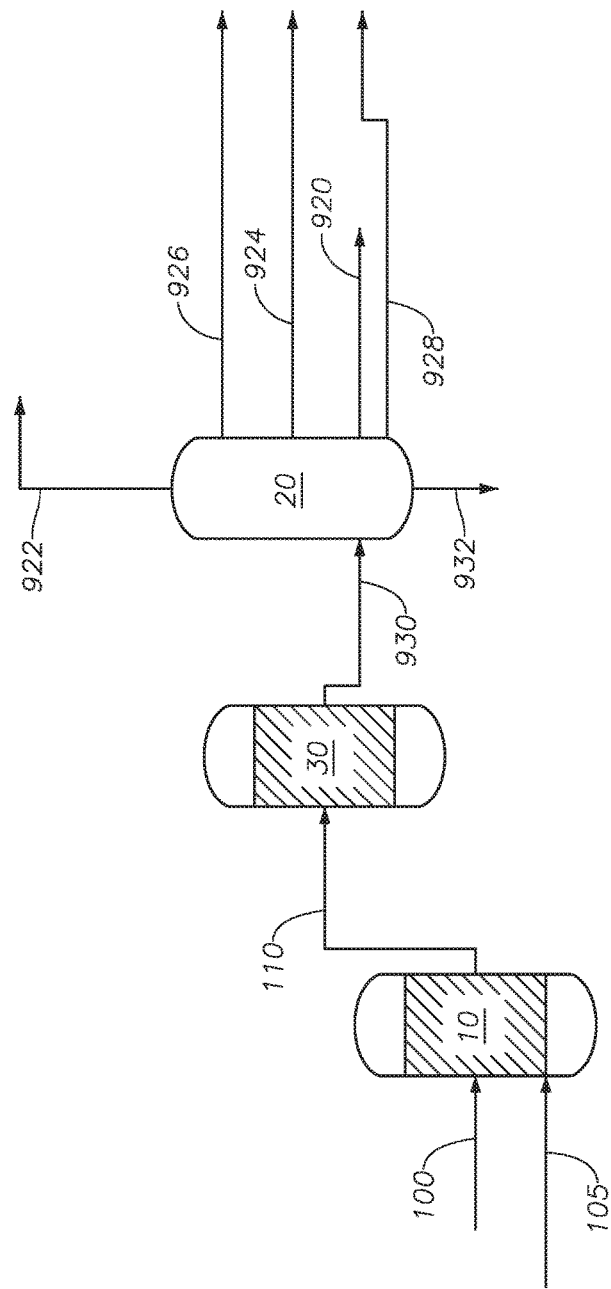
FIG. 9 provides a process diagram of a process in the absence of a splitter unit between a dealkylation reactor and transalkylation reactor.

Example 7 was a comparative example in the absence of a splitter unit between the dealkylation reactor and transalkylation reactor with reference to FIG. 9. Heavy reformate feed 100, having the composition in Table 19, was introduced to dealkylation reactor 10 along with hydrogen feed 105. The flow rate of hydrogen feed 105 was 138.6 kg/hr with 66.5 kg/hr hydrogen gas and 72.0 kg/hr light hydrocarbons.

TABLE 19

Composition of heavy reformate feed 100

| Component | Composition, kg/hr | Composition, wt % |
|---|---|---|
| Mass Flow | 1000.0 | 100 |
| Hydrogen | 0 | 0.0 |

TABLE 19-continued

Composition of heavy reformate feed 100

| Component | Composition, kg/hr | Composition, wt % |
|---|---|---|
| Light gases | 0 | 0.0 |
| Benzene | 0 | 0.0 |
| Toluene | 0 | 0.0 |
| Ethylbenzene | 0.5 | 0.0 |
| Mixed xylenes | 51.8 | 5.2 |
| m-xylene | 31.8 | 3.2 |
| o-xylene | 10.0 | 1.0 |
| p-xylene | 10.0 | 1.0 |
| C9 aromatics total | 801.6 | 80.2 |
| Trimethylbenzene | 565.5 | 56.5 |
| Methylethylbenzene | 210.9 | 21.1 |
| Propylbenzene | 25.2 | 2.5 |
| C10+ aromatics | 146.2 | 14.6 |

Dealkylation reactor 10 was at a temperature of 400 deg C. and a pressure of 30 bar (3000 kPa). The whsv was 4.2 $hr^{-1}$. The ratio of hydrogen gas ($H_2$) to hydrocarbons was 4:1 (mol/mol). The catalyst was a 3-dimensional zeolite-based dealkylation catalyst. The composition of dealkylation effluent 110 is shown in Table 20.

TABLE 20

Composition of dealkylation effluent 110

| Component | Composition, kg/hr | Composition, wt % calculated without hydrogen gas |
|---|---|---|
| Mass Flow | 1138.6 | — |
| Hydrogen | 63.0 | — |
| Light gases | 106.5 | 9.9 |
| Benzene | 26.8 | 2.5 |
| Toluene | 174.9 | 16.3 |
| Ethylbenzene | 0.4 | 0.0 |
| Mixed xylenes | 177.5 | 16.5 |
| m-xylene | 102.2 | 9.5 |
| o-xylene | 39.9 | 3.7 |
| p-xylene | 35.4 | 3.3 |
| C9 aromatics total | 506.4 | 47.1 |
| Trimethylbenzene | 503.8 | 46.8 |
| Methylethylbenzene | 2.5 | 0.2 |

TABLE 20-continued

Composition of dealkylation effluent 110

| Component | Composition, kg/hr | Composition, wt % calculated without hydrogen gas |
|---|---|---|
| Propylbenzene | 0.0 | 0.0 |
| C10+ aromatics | 83.1 | 7.7 |

Dealkylation effluent 110 was introduced to transalkylation reactor 30. Transalkylation reactor 30 was at a temperature of 400 deg C. and a pressure of 30 bar (3000 kPa). The whsv was 4.2 h$^{-1}$. The ratio of hydrogen gas (H$_2$) to hydrocarbons is 4:1 (mol/mol). The catalyst was a 1-dimensional zeolite-based transalkylation catalyst. The transalkylation catalyst was not the same as the dealkylation catalyst. Transalkylation product 930 was introduced to splitter unit 20 which separated transalkylation product 930 into its component parts: mixed xylenes fraction 920, light gases fraction 922, toluene fraction 924, benzene fraction 926, C9 aromatics fraction 928, and C10+ aromatics fraction 932. The composition of various streams are shown in Table 21.

TABLE 21

Composition of Streams

Composition, kg/hr (wt % calculated without hydrogen gas)

| Component | Stream 930 | Stream 920 | Stream 922 | Stream 924 | Stream 926 | Stream 928 | Stream 932 |
|---|---|---|---|---|---|---|---|
| Mass Flow | 1138.6 | 425.9 | 155.5 | 308.1 | 42.1 | 161.3 | 45.7 |
| Hydrogen | 60.8 | 0.0 | 60.8 | 0.0 | 0.0 | 0.0 | 0.0 |
| Light hydrocarbons | 94.7 (8.8) | 0.0 | 94.7 (100) | 0.0 | 0.0 | 0.0 | 0.0 |
| Benzene | 42.1 (3.9) | 0.0 | 0.0 | 0.0 | 42.1 (100) | 0.0 | 0.0 |
| Toluene | 308.1 (28.6) | 0.0 | 0.0 | 308.1 (100) | 0.0 | 0.0 | 0.0 |
| Ethylbenzene | 20.1 (1.9) | 20.1 (4.7) | 0.0 | 0.0 | 0.0 | 0.0 | 0.0 |
| Mixed xylenes | 405.8 (37.6) | 405.8 (95.3) | 0.0 | 0.0 | 0.0 | 0.0 | 0.0 |
| m-xylene | 233.6 (21.7) | 233.6 (54.9) | — | — | — | — | — |
| o-xylene | 91.2 (8.5) | 91.2 (21.4) | — | — | — | — | — |
| p-xylene | 80.9 (7.5) | 80.9 (19.0) | — | — | — | — | — |
| C9 aromatics total | 161.3 (15.0) | 0.0 | 0.0 | 0.0 | 0.0 | 161.3 (100.0) | 0.0 |
| Trimethylbenzene | 160.2 (14.9) | — | — | — | — | 160.2 (99.3) | — |
| Methylethylbenzene | 1.1 (0.1) | — | — | — | — | 1.1 (0.7) | — |
| Propylbenzene | 0.0 | — | — | — | — | 0.0 | — |
| C10+ aromatics | 45.7 (4.2) | 0.0 | 0.0 | 0.0 | 0.0 | 0.0 | 45.7 (100) |

The production of mixed xylenes was 405.8 kg/hr. The overall conversion of trimethylbenzene is 72 wt %.

Comparing the production rate of mixed xylenes in Example 4 and Example 7 shows that the addition of a splitter unit and the associated process stream configuration changes unexpectedly and advantageously increases the production rate of mixed xylenes by about 100%.

Example 8

Example 8 illustrates the xylene production process with energy optimization with reference to FIG. 10. Example 8 was simulated using Aspen Plus®. The compositions and temperatures of the streams are shown in Table 22.

TABLE 22

Stream temperature and composition

| | | 100 | 200 | 105 | 205 | 210 | 215 | 110 | 220 | 225 | 230 |
|---|---|---|---|---|---|---|---|---|---|---|---|
| Temperature | C. | 44 | 115 | 38 | 88 | 344 | 400 | 400 | 130 | 96 | 42 |
| Mass Flow | kg/hr | 1000 | 1000 | 137 | 1137 | 1137 | 1137 | 1137 | 1137 | 1137 | 1137 |
| Hydrogen | kg/hr | 0 | 0 | 66 | 66 | 66 | 66 | 62 | 62 | 62 | 62 |
| C1-C5 | kg/hr | 0 | 0 | 71 | 71 | 71 | 71 | 155 | 155 | 155 | 155 |
| Benzene | kg/hr | 0 | 0 | 0 | 0 | 0 | 0 | 25 | 25 | 25 | 25 |
| Toluene | kg/hr | 0 | 0 | 0 | 0 | 0 | 0 | 169 | 169 | 169 | 169 |
| Ethylbenzene | kg/hr | 0 | 0 | 0 | 0 | 0 | 0 | 0 | 0 | 0 | 0 |
| Xylenes Total | kg/hr | 0 | 0 | 0 | 0 | 0 | 0 | 116 | 116 | 116 | 116 |
| m-xylene | kg/hr | 0 | 0 | 0 | 0 | 0 | 0 | 67 | 67 | 67 | 67 |
| o-xylene | kg/hr | 0 | 0 | 0 | 0 | 0 | 0 | 26 | 26 | 26 | 26 |
| p-xylene | kg/hr | 0 | 0 | 0 | 0 | 0 | 0 | 23 | 23 | 23 | 23 |
| C9 aromatics Total | kg/hr | 846 | 846 | 0 | 846 | 846 | 846 | 534 | 534 | 534 | 534 |
| MEB | kg/hr | 223 | 223 | 0 | 223 | 223 | 223 | 223 | 223 | 223 | 223 |
| TMB | kg/hr | 597 | 597 | 0 | 597 | 597 | 597 | 531 | 531 | 531 | 531 |
| Propylbenzene | kg/hr | 27 | 27 | 0 | 27 | 27 | 27 | 0 | 0 | 0 | 0 |

TABLE 22-continued

Stream temperature and composition

| | | | | | | | | | | | |
|---|---|---|---|---|---|---|---|---|---|---|---|
| C10+ | kg/hr | 154 | 154 | 0 | 154 | 154 | 154 | 77 | 77 | 77 | 77 |
| Total HC Flow | kg/hr | 1000 | 1000 | 71 | 1071 | 1071 | 1071 | 1075 | 1075 | 1075 | 1075 |

| | | 240 | 247 | 140 | 126 | 120 | 128 | 132 | 124 | 135 | 250 |
|---|---|---|---|---|---|---|---|---|---|---|---|
| Temperature | C. | 42 | 115 | 115 | 115 | 150 | 150 | 115 | 150 | 38 | 137 |
| Mass Flow | kg/hr | 949 | 949 | 72 | 37 | 765 | 1131 | 65 | 586 | 20 | 1737 |
| Hydrogen | kg/hr | 0 | 0 | 0 | 0 | 0 | 0 | 0 | 0 | 20 | 20 |
| C1-C5 | kg/hr | 35 | 35 | 72 | 0 | 0 | 0 | 0 | 0 | 0 | 0 |
| Benzene | kg/hr | 24 | 24 | 0 | 37 | 0 | 0 | 0 | 37 | 0 | 37 |
| Toluene | kg/hr | 166 | 166 | 0 | 0 | 0 | 0 | 0 | 549 | 0 | 549 |
| Ethylbenzene | kg/hr | 0 | 0 | 0 | 0 | 30 | 0 | 0 | 0 | 0 | 0 |
| Xylenes Total | kg/hr | 115 | 115 | 0 | 0 | 735 | 0 | 0 | 0 | 0 | 0 |
| m-xylene | kg/hr | 66 | 66 | 0 | 0 | 423 | 0 | 0 | 0 | 0 | 0 |
| o-xylene | kg/hr | 26 | 26 | 0 | 0 | 165 | 0 | 0 | 0 | 0 | 0 |
| p-xylene | kg/hr | 23 | 23 | 0 | 0 | 146 | 0 | 0 | 0 | 0 | 0 |
| C9 aromatics Total | kg/hr | 533 | 533 | 0 | 0 | 0 | 1065 | 0 | 0 | 0 | 1065 |
| MEB | kg/hr | 3 | 3 | 0 | 0 | 0 | 5 | 0 | 0 | 0 | 5 |
| TMB | kg/hr | 530 | 530 | 0 | 0 | 0 | 1060 | 0 | 0 | 0 | 1060 |
| Propylbenzene | kg/hr | 0 | 0 | 0 | 0 | 0 | 0 | 0 | 0 | 0 | 0 |
| C10+ | kg/hr | 77 | 77 | 0 | 0 | 0 | 65 | 65 | 0 | 0 | 65 |
| Total HC Flow | kg/hr | 949 | 949 | 72 | 37 | 765 | 1131 | 65 | 586 | 0 | 1717 |

| | | 255 | 260 | 130 | 265 | 270 | 275 | 280 | 285 | 290 | 295 |
|---|---|---|---|---|---|---|---|---|---|---|---|
| Temperature | C. | 380 | 400 | 400 | 151 | 93 | 40 | 40 | 115 | 60 | 40 |
| Mass Flow | kg/hr | 1737 | 1737 | 1737 | 1737 | 1737 | 1737 | 1707 | 1707 | 765 | 765 |
| Hydrogen | kg/hr | 20 | 20 | 16 | 16 | 16 | 16 | 0 | 0 | 0 | 0 |
| C1-C5 | kg/hr | 0 | 0 | 50 | 50 | 50 | 50 | 37 | 37 | 0 | 0 |
| Benzene | kg/hr | 37 | 37 | 52 | 52 | 52 | 52 | 51 | 51 | 0 | 0 |
| Toluene | kg/hr | 549 | 549 | 384 | 384 | 384 | 384 | 383 | 383 | 0 | 0 |
| Ethylbenzene | kg/hr | 0 | 0 | 30 | 30 | 30 | 30 | 30 | 30 | 30 | 30 |
| Xylenes Total | kg/hr | 0 | 0 | 620 | 620 | 620 | 620 | 619 | 619 | 735 | 735 |
| m-xylene | kg/hr | 0 | 0 | 357 | 357 | 357 | 357 | 357 | 357 | 423 | 423 |
| o-xylene | kg/hr | 0 | 0 | 139 | 139 | 139 | 139 | 139 | 139 | 165 | 165 |
| p-xylene | kg/hr | 0 | 0 | 124 | 124 | 124 | 124 | 123 | 123 | 146 | 146 |
| C9 aromatics Total | kg/hr | 1065 | 1065 | 533 | 533 | 533 | 533 | 533 | 533 | 0 | 0 |
| MEB | kg/hr | 5 | 5 | 3 | 3 | 3 | 3 | 3 | 3 | 0 | 0 |
| TMB | kg/hr | 1060 | 530 | 530 | 530 | 530 | 530 | 530 | 0 | 0 | 0 |
| Propylbenzene | kg/hr | 0 | 0 | 0 | 0 | 0 | 0 | 0 | 0 | 0 | 0 |
| C10+ | kg/hr | 65 | 65 | 53 | 53 | 53 | 53 | 53 | 53 | 0 | 0 |
| Total HC Flow | kg/hr | 1717 | 1717 | 1721 | 1721 | 1721 | 1721 | 1707 | 1707 | 765 | 765 |

Example 9

Example 9 illustrates the xylene production process with energy optimization with reference to FIG. 11 and FIG. 10. Example 9 was simulated using Aspen Plus®. The compositions and temperatures of the streams are shown in Table 23.

TABLE 23

Stream temperature and compositions.

| | | 100 | 200 | 105 | 205 | 207 | 209 | 210 | 215 | 110 | 220 | 225 |
|---|---|---|---|---|---|---|---|---|---|---|---|---|
| Temperature | C. | 44 | 78 | 38 | 64 | 80 | 108 | 369 | 400 | 400 | 125 | 90 |
| Mass Flow | kg/hr | 1000 | 1000 | 137 | 1137 | 1137 | 1137 | 1137 | 1137 | 1137 | 1137 | 1137 |
| Hydrogen | kg/hr | 0 | 0 | 66 | 66 | 66 | 66 | 66 | 66 | 62 | 62 | 62 |
| C1-C5 | kg/hr | 0 | 0 | 71 | 71 | 71 | 71 | 71 | 71 | 155 | 155 | 155 |
| Benzene | kg/hr | 0 | 0 | 0 | 0 | 0 | 0 | 0 | 0 | 25 | 25 | 25 |
| Toluene | kg/hr | 0 | 0 | 0 | 0 | 0 | 0 | 0 | 0 | 169 | 169 | 169 |
| Ethylbenzene | kg/hr | 0 | 0 | 0 | 0 | 0 | 0 | 0 | 0 | 0 | 0 | 0 |
| Xylenes Total | kg/hr | 0 | 0 | 0 | 0 | 0 | 0 | 0 | 0 | 116 | 116 | 116 |
| m-xylene | kg/hr | 0 | 0 | 0 | 0 | 0 | 0 | 0 | 0 | 67 | 67 | 67 |
| o-xylene | kg/hr | 0 | 0 | 0 | 0 | 0 | 0 | 0 | 0 | 26 | 26 | 26 |
| p-xylene | kg/hr | 0 | 0 | 0 | 0 | 0 | 0 | 0 | 0 | 23 | 23 | 23 |
| C9 aromatics Total | kg/hr | 846 | 846 | 0 | 846 | 846 | 846 | 846 | 846 | 534 | 534 | 534 |
| MEB | kg/hr | 223 | 223 | 0 | 223 | 223 | 223 | 223 | 223 | 3 | 3 | 3 |
| TMB | kg/hr | 597 | 597 | 0 | 597 | 597 | 597 | 597 | 597 | 531 | 531 | 531 |
| Propylbenzene | kg/hr | 27 | 27 | 0 | 27 | 27 | 27 | 27 | 27 | 0 | 0 | 0 |

TABLE 23-continued

Stream temperature and compositions.

| | | | | | | | | | | | | |
|---|---|---|---|---|---|---|---|---|---|---|---|---|
| C10+ | kg/hr | 154 | 154 | 0 | 154 | 154 | 154 | 154 | 154 | 77 | 77 | 77 |
| Total HC Flow | kg/hr | 1000 | 1000 | 71 | 1071 | 1071 | 1071 | 1071 | 1071 | 1075 | 1075 | 1075 |

| | | 227 | 230 | 240 | 247 | 140 | 126 | 120 | 128 | 132 | 124 | 135 | 250 |
|---|---|---|---|---|---|---|---|---|---|---|---|---|---|
| Temperature | C. | 76 | 42 | 42 | 115 | 115 | 115 | 150 | 150 | 115 | 150 | 38 | 137 |
| Mass Flow | kg/hr | 1137 | 1137 | 949 | 949 | 72 | 37 | 765 | 1131 | 65 | 586 | 20 | 1737 |
| Hydrogen | kg/hr | 62 | 62 | 0 | 0 | 0 | 0 | 0 | 0 | 0 | 0 | 20 | 20 |
| C1-C5 | kg/hr | 155 | 155 | 35 | 35 | 72 | 0 | 0 | 0 | 0 | 0 | 0 | 0 |
| Benzene | kg/hr | 25 | 25 | 24 | 24 | 0 | 37 | 0 | 0 | 0 | 37 | 0 | 37 |
| Toluene | kg/hr | 169 | 169 | 166 | 166 | 0 | 0 | 0 | 0 | 0 | 549 | 0 | 549 |
| Ethylbenzene | kg/hr | 0 | 0 | 0 | 0 | 0 | 0 | 30 | 0 | 0 | 0 | 0 | 0 |
| Xylenes Total | kg/hr | 116 | 116 | 115 | 115 | 0 | 0 | 735 | 0 | 0 | 0 | 0 | 0 |
| m-xylene | kg/hr | 67 | 67 | 66 | 66 | 0 | 0 | 423 | 0 | 0 | 0 | 0 | 0 |
| o-xylene | kg/hr | 26 | 26 | 26 | 26 | 0 | 0 | 165 | 0 | 0 | 0 | 0 | 0 |
| p-xylene | kg/hr | 23 | 23 | 23 | 23 | 0 | 0 | 146 | 0 | 0 | 0 | 0 | 0 |
| C9 aromatics Total | kg/hr | 534 | 534 | 533 | 533 | 0 | 0 | 0 | 1065 | 0 | 0 | 0 | 1065 |
| MEB | kg/hr | 3 | 3 | 3 | 3 | 0 | 0 | 0 | 5 | 0 | 0 | 0 | 5 |
| TMB | kg/hr | 531 | 531 | 530 | 530 | 0 | 0 | 0 | 1060 | 0 | 0 | 0 | 1060 |
| Propylbenzene | kg/hr | 0 | 0 | 0 | 0 | 0 | 0 | 0 | 0 | 0 | 0 | 0 | 0 |
| C10+ | kg/hr | 77 | 77 | 77 | 77 | 0 | 0 | 0 | 65 | 65 | 0 | 0 | 65 |
| Total HC Flow | kg/hr | 1075 | 1075 | 949 | 949 | 72 | 37 | 765 | 1131 | 65 | 586 | 0 | 1717 |

| | | 255 | 260 | 130 | 265 | 270 | 272 | 275 | 280 | 285 | 292 | 295 |
|---|---|---|---|---|---|---|---|---|---|---|---|---|
| Temperature | C. | 383 | 400 | 400 | 148 | 89 | 72 | 40 | 40 | 115 | 90 | 40 |
| Mass Flow | kg/hr | 1737 | 1737 | 1737 | 1737 | 1737 | 1737 | 1737 | 1707 | 1707 | 765 | 765 |
| Hydrogen | kg/hr | 20 | 20 | 16 | 16 | 16 | 16 | 16 | 0 | 0 | 0 | 0 |
| C1-C5 | kg/hr | 0 | 0 | 50 | 50 | 50 | 50 | 50 | 37 | 37 | 0 | 0 |
| Benzene | kg/hr | 37 | 37 | 52 | 52 | 52 | 52 | 52 | 51 | 51 | 0 | 0 |
| Toluene | kg/hr | 549 | 549 | 384 | 384 | 384 | 384 | 384 | 383 | 383 | 0 | 0 |
| Ethylbenzene | kg/hr | 0 | 0 | 30 | 30 | 30 | 30 | 30 | 30 | 30 | 30 | 30 |
| Xylenes Total | kg/hr | 0 | 0 | 620 | 620 | 620 | 620 | 620 | 619 | 619 | 735 | 735 |
| m-xylene | kg/hr | 0 | 0 | 357 | 357 | 357 | 357 | 357 | 357 | 357 | 423 | 423 |
| o-xylene | kg/hr | 0 | 0 | 139 | 139 | 139 | 139 | 139 | 139 | 139 | 165 | 165 |
| p-xylene | kg/hr | 0 | 0 | 124 | 124 | 124 | 124 | 124 | 123 | 123 | 146 | 146 |
| C9 aromatics Total | kg/hr | 1065 | 1065 | 533 | 533 | 533 | 533 | 533 | 533 | 533 | 0 | 0 |
| MEB | kg/hr | 5 | 5 | 3 | 3 | 3 | 3 | 3 | 3 | 3 | 0 | 0 |
| TMB | kg/hr | 1060 | 1060 | 530 | 530 | 530 | 530 | 530 | 530 | 530 | 0 | 0 |
| Propylbenzene | kg/hr | 0 | 0 | 0 | 0 | 0 | 0 | 0 | 0 | 0 | 0 | 0 |
| C10+ | kg/hr | 65 | 65 | 53 | 53 | 53 | 53 | 53 | 53 | 53 | 0 | 0 |
| Total HC Flow | kg/hr | 1717 | 1717 | 1721 | 1721 | 1721 | 1721 | 1721 | 1707 | 1707 | 765 | 765 |

Example 10

Figure 12:
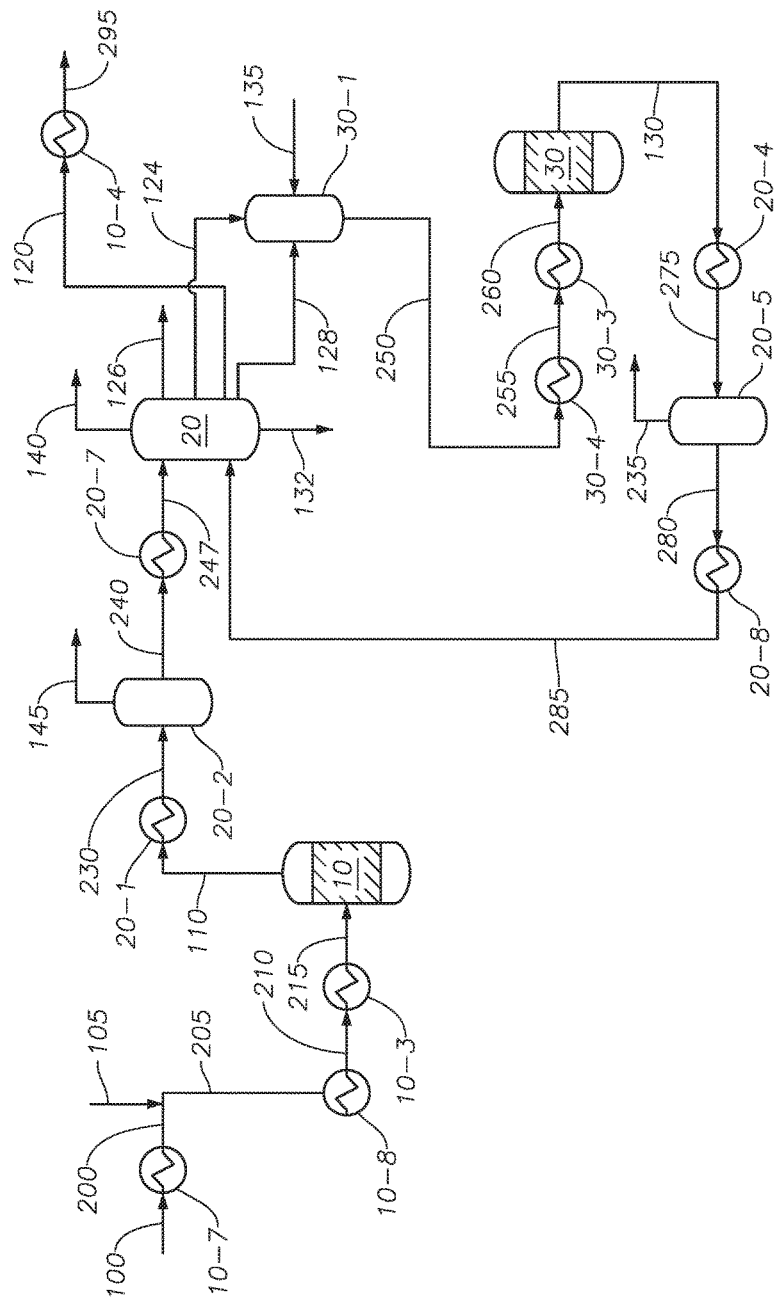
FIG. 12 provides a process diagram of an embodiment of the process with energy optimization.

Example 10 is a comparative example that illustrates a xylene production process in the absence of energy optimization with reference to FIG. 12 and FIG. 10. Example 9 was simulated using Aspen Plus®.

In a process according to FIG. 12, heavy reformate 100 is heated in first process heater 10-7 to produce hot feed stream 200. Hot feed stream 200 and hydrogen feed 105 are mixed to produce mixed feed 205. Mixed feed 205 is heated in second process heater 10-8 to produce hot mixed feed 210. Hot mixed feed 210 is heated in feed fired heater 10-3 to produce hot reactor feed 215. Hot reactor feed 215 is reacted in dealkylation reactor 10 to produce dealkylation effluent 110. Dealkylation effluent 110 is cooled in effluent cooler 20-1 to produced mixed effluent stream 230. Hydrogen in mixed effluent stream 230 is separated in effluent separator 20-2 to produce produced hydrogen 145 and separated effluent 240. Separated effluent 240 is heated in third process heater 20-7 to produce dealkylation splitter feed 247. Dealkylation splitter feed 247 is separated in splitter unit 20 to produce light gas product 140, toluene stream 124, benzene stream 126, C9 aromatics stream 128, C10+ aromatics stream 132, and mixed xylene stream 120. Toluene stream 124, C9 aromatics stream 128, and hydrogen stream 135 are mixed in mixer 30-1 to produce mixed transalkylation feed 250. Mixed transalkylation feed 250 is heated in fourth process heater 30-4 to produce hot transalkylation feed 255. Hot transalkylation feed 255 is heated in transalkylation fired heater 30-3 to produce transalkylation feed 260. Transalkylation feed 260 is reacted in transalkylation reactor 30 to produce transalkylation effluent 130. Transalkylation effluent 130 is cooled in transalkylation cooler 20-4 to produce cooled mixed effluent 275. Light gases stream 235 are separated in transalkylation separator 20-5 to produce separated transalkylation effluent 280. Separated transalkylation effluent 280 can beis heated in fifth process heater 20-8 to produce transalkylation splitter feed 285. Mixed xylene stream 120 can beis cooled in xylene cooler 10-4 to produce mixed xylene product 295. The stream temperature and compositions are in Table 24.

TABLE 24

Stream temperature and compositions.

|  |  | 100 | 200 | 105 | 205 | 210 | 215 | 110 | 230 | 240 | 247 | 140 | 126 | 120 |
|---|---|---|---|---|---|---|---|---|---|---|---|---|---|---|
| Temperature | C. | 44 | 115 | 38 | 87 | 200 | 400 | 400 | 42 | 42 | 115 | 115 | 115 | 150 |
| Mass Flow | kg/hr | 1000 | 1000 | 137 | 1137 | 1137 | 1137 | 1137 | 1137 | 949 | 949 | 72 | 37 | 765 |
| Hydrogen | kg/hr | 0 | 0 | 66 | 66 | 66 | 66 | 62 | 62 | 0 | 0 | 0 | 0 | 0 |
| C1-C5 | kg/hr | 0 | 0 | 71 | 71 | 71 | 71 | 155 | 155 | 35 | 35 | 72 | 0 | 0 |
| Benzene | kg/hr | 0 | 0 | 0 | 0 | 0 | 0 | 25 | 25 | 24 | 24 | 0 | 37 | 0 |
| Toluene | kg/hr | 0 | 0 | 0 | 0 | 0 | 0 | 169 | 169 | 166 | 166 | 0 | 0 | 0 |
| Ethylbenzene | kg/hr | 0 | 0 | 0 | 0 | 0 | 0 | 0 | 0 | 0 | 0 | 0 | 0 | 30 |
| Xylenes Total | kg/hr | 0 | 0 | 0 | 0 | 0 | 0 | 116 | 116 | 115 | 115 | 0 | 0 | 735 |
| m-xylene | kg/hr | 0 | 0 | 0 | 0 | 0 | 0 | 67 | 67 | 66 | 66 | 0 | 0 | 423 |
| o-xylene | kg/hr | 0 | 0 | 0 | 0 | 0 | 0 | 26 | 26 | 26 | 26 | 0 | 0 | 165 |
| p-xylene | kg/hr | 0 | 0 | 0 | 0 | 0 | 0 | 23 | 23 | 23 | 23 | 0 | 0 | 146 |
| C9 aromatics Total | kg/hr | 846 | 846 | 0 | 846 | 846 | 846 | 534 | 534 | 533 | 533 | 0 | 0 | 0 |
| MEB | kg/hr | 223 | 223 | 0 | 223 | 223 | 223 | 3 | 3 | 3 | 3 | 0 | 0 | 0 |
| TMB | kg/hr | 597 | 597 | 0 | 597 | 597 | 597 | 531 | 531 | 530 | 530 | 0 | 0 | 0 |
| Propylbenzene | kg/hr | 27 | 27 | 0 | 27 | 27 | 27 | 0 | 0 | 0 | 0 | 0 | 0 | 0 |
| C10+ | kg/hr | 154 | 154 | 0 | 154 | 154 | 154 | 77 | 77 | 77 | 77 | 0 | 0 | 0 |
| Total HC Flow | kg/hr | 1000 | 1000 | 71 | 1071 | 1071 | 1071 | 1075 | 1075 | 949 | 949 | 72 | 37 | 765 |

|  |  | 128 | 132 | 124 | 135 | 250 | 255 | 260 | 130 | 275 | 280 | 285 | 295 |
|---|---|---|---|---|---|---|---|---|---|---|---|---|---|
| Temperature | C. | 150 | 115 | 150 | 38 | 137 | 200 | 400 | 400 | 40 | 40 | 115 | 40 |
| Mass Flow | kg/hr | 1131 | 65 | 586 | 20 | 1737 | 1737 | 1737 | 1737 | 1737 | 1707 | 1707 | 765 |
| Hydrogen | kg/hr | 0 | 0 | 0 | 20 | 20 | 20 | 20 | 16 | 16 | 0 | 0 | 0 |
| C1-C5 | kg/hr | 0 | 0 | 0 | 0 | 0 | 0 | 0 | 50 | 50 | 37 | 37 | 0 |
| Benzene | kg/hr | 0 | 0 | 37 | 0 | 37 | 37 | 37 | 52 | 52 | 51 | 51 | 0 |
| Toluene | kg/hr | 0 | 0 | 549 | 0 | 549 | 549 | 549 | 384 | 384 | 383 | 383 | 0 |
| Ethylbenzene | kg/hr | 0 | 0 | 0 | 0 | 0 | 0 | 0 | 30 | 30 | 30 | 30 | 30 |
| Xylenes Total | kg/hr | 0 | 0 | 0 | 0 | 0 | 0 | 0 | 620 | 620 | 619 | 619 | 735 |
| m-xylene | kg/hr | 0 | 0 | 0 | 0 | 0 | 0 | 0 | 357 | 357 | 357 | 357 | 423 |
| o-xylene | kg/hr | 0 | 0 | 0 | 0 | 0 | 0 | 0 | 139 | 139 | 139 | 139 | 165 |
| p-xylene | kg/hr | 0 | 0 | 0 | 0 | 0 | 0 | 0 | 124 | 124 | 123 | 123 | 146 |
| C9 aromatics Total | kg/hr | 1065 | 0 | 0 | 0 | 1065 | 1065 | 1065 | 533 | 533 | 533 | 533 | 0 |
| MEB | kg/hr | 5 | 0 | 0 | 0 | 5 | 5 | 5 | 3 | 3 | 3 | 3 | 0 |
| TMB | kg/hr | 1060 | 0 | 0 | 0 | 1060 | 1060 | 1060 | 530 | 530 | 530 | 530 | 0 |
| Propylbenzene | kg/hr | 0 | 0 | 0 | 0 | 0 | 0 | 0 | 0 | 0 | 0 | 0 | 0 |
| C10+ | kg/hr | 65 | 65 | 0 | 0 | 65 | 65 | 65 | 53 | 53 | 53 | 53 | 0 |
| Total HC Flow | kg/hr | 1131 | 65 | 586 | 0 | 1717 | 1717 | 1717 | 1721 | 1721 | 1707 | 1707 | 765 |

Aspen Energy Analyzer was used to determine values for the heat exchanger network design in each of Examples 8, 9, and 10. The values are shown in Table 25.

TABLE 25

Heat exchanger values

| Example | FIG. | Area (m$^2$) | Shells | Heating (kJ/h) | Cooling (kJ/h) |
|---|---|---|---|---|---|
| 8 | 10 | 216 | 35 | 291,113 | 397,858 |
| 9 | 11 | 369 | 47 | 185,694 | 292428 |
| 10 | 12 | 37 | 18 | 3,432,166 | 3,538,909 |

As can be seen in Table 25, the process according to Example 10 requires 91.5% more heat input than the process of Example 8 and 94.5% more heat input than the process of Example 9. The process according to Example 10 requires 88.7% more cooling input than the process of Example 8 and 91.7% more cooling input.

Although the embodiments have been described in detail, it should be understood that various changes, substitutions, and alterations can be made without departing from the principle and scope. Accordingly, the scope of the present embodiments should be determined by the following claims and their appropriate legal equivalents.

There various elements described can be used in combination with all other elements described here unless otherwise indicated.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed here as from about one particular value to about another particular value and are inclusive unless otherwise indicated. When such a range is expressed, it is to be understood that another embodiment is from the one particular value to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made here.

As used here and in the appended claims, the words "comprise," "has," and "include" and all grammatical variations thereof are each intended to have an open, non-limiting meaning that does not exclude additional elements or steps.

That which is claimed is:

1. A method for producing mixed xylenes from a heavy reformate feed, the method comprising the steps of:
    introducing the heavy reformate feed to a feed exchanger to produce a hot feed stream, wherein the feed exchanger increases the temperature of the heavy reformate feed, wherein the heavy reformate comprises aromatic hydrocarbons with nine or more carbon atoms (C9+ aromatics), wherein the hydrogen feed comprises hydrogen gas;

mixing the hot feed stream and a hydrogen feed to produce a mixed feed;
increasing a temperature of the mixed feed in a feed-effluent exchanger to produce a hot mixed feed, wherein a temperature of the hot mixed feed is between 324° C. and 344° C.;
increasing the temperature of the hot mixed feed in a feed fired heater to produce a hot reactor feed, wherein a temperature of the hot reactor feed is between 380° C. and 400° C.;
introducing the hot reactor feed to a dealkylation reactor, wherein the dealkylation reactor comprises a dealkylation catalyst;
reacting the heavy reformate feed with the hydrogen gas in the presence of the dealkylation catalyst in the dealkylation reactor to produce a dealkylation effluent, wherein the dealkylation reactor is at a dealkylation temperature, wherein the dealkylation reactor is at a dealkylation pressure, wherein the dealkylation reactor has a liquid hourly space velocity;
reducing a temperature of the dealkylation effluent in the feed-effluent exchanger to produce a cooled effluent stream, wherein a temperature of the cooled effluent stream is between 115° C. and 145° C.;
reducing the temperature of the cooled effluent in an effluent-separator exchanger to produce an effluent stream, wherein a temperature of the effluent stream is between 80° C. and 110° C.;
reducing the temperature of the effluent stream in an effluent cooler to produce a mixed effluent stream, wherein a temperature of the mixed effluent stream is between 38° C. and 47° C.;
separating the mixed effluent stream in an effluent separator to produce a produced hydrogen and a separated effluent, wherein the produced hydrogen comprises hydrogen;
increasing a temperature of the separated effluent in the effluent-separator exchanger to produce a dealkylation splitter feed, wherein a temperature of the dealkylation splitter feed is between 100° C. and 130° C.;
introducing the dealkylation splitter feed to a splitter unit, where the dealkylation effluent comprises light gases, toluene, benzene, mixed xylenes, and C9+ aromatics;
separating the dealkylation effluent into a light gas product, a toluene stream, a benzene stream, a C9 aromatics stream, a C10+ aromatics stream, and a mixed xylene stream in the splitter unit, wherein the light gas stream comprises light hydrocarbons and hydrogen, wherein the toluene stream comprises toluene, wherein the benzene stream comprises benzene, wherein the mixed xylene stream comprises mixed xylenes, wherein the C9 stream comprises C9 aromatics, wherein the C10+ aromatics stream comprises C10+ aromatics;
mixing the toluene stream, the C9 aromatics stream, and a hydrogen stream in a mixer to produce a mixed transalkylation feed;
increasing a temperature of the mixed transalkylation feed in a C9-effluent heater to produce a hot transalkylation feed, wherein a temperature of the hot transalkylation feed is between 330° C. and 390° C.;
increasing the temperature of the hot transalkylation feed in a transalkylation fired heater to produce a transalkylation feed, wherein a temperature of the transalkylation feed is between 380° C. and 400° C.;
introducing the transalkylation feed to a transalkylation reactor, wherein the transalkylation reactor comprises a transalkylation catalyst, wherein the hydrogen stream comprises hydrogen gas;
reacting the toluene stream and the C9 aromatics stream in the presence of the transalkylation catalyst to produce a transalkylation effluent, wherein the transalkylation reactor is at a transalkylation temperature, wherein the transalkylation reactor is at a transalkylation pressure, wherein the transalkylation reactor has a liquid hourly space velocity; reducing a temperature of the transalkylation effluent in the C9-effluent heater to produce a cooled transalkylation effluent, wherein a temperature of the cooled transalkylation effluent between 136° C. and 166° C.; reducing the temperature of the transalkylation effluent in an effluent-transalkylation exchanger to produce a cooled effluent, wherein a temperature of the cooled effluent is between 83° C. and 103° C.;
reducing the temperature of the cooled effluent in a transalkylation cooler to produce a cooled mixed effluent, wherein a temperature of the cooled mixed effluent is between 35° C. and 45° C.;
separating the cooled mixed effluent in a transalkylation separator to produce a separated transalkylation effluent and a light gases stream; increasing a temperature of the separated transalkylation effluent in the effluent-transalkylation exchanger to produce a transalkylation splitter feed, wherein a temperature of the transalkylation splitter feed is between 105° C. and 125° C.; introducing the transalkylation splitter feed to the splitter unit, wherein the transalkylation effluent comprises light gases, toluene, benzene, mixed xylenes, and C9+ aromatics; separating the transalkylation splitter feed in the splitter unit such that mixed xylenes in the transalkylation splitter feed exit the splitter unit as part of the mixed xylene stream; reducing a temperature of the mixed xylene stream in the feed exchanger to produce a cooled mixed stream, wherein a temperature of the cooled mixed stream is between 55° C. and 65° C.; and
reducing the temperature of the cooled mixed stream in a xylene cooler to produce a mixed xylene product, wherein a temperature of the mixed xylene product is between 30° C. and 50° C.

2. The method of claim 1, wherein the feed exchanger is a cross process exchanger, wherein the feed exchanger is configured to transfer heat from the mixed xylene stream to the heavy reformate feed.

3. The method of claim 1, wherein the feed-effluent exchanger is a cross process exchanger, wherein the feed-effluent exchanger is configured to transfer heat from the dealkylation effluent to the mixed feed.

4. The method of claim 1, wherein the effluent-separator exchanger is a cross process exchanger, wherein the effluent-separator exchanger is configured to transfer heat from the cooled effluent stream to the separated effluent.

5. The method of claim 1, wherein the C9-effluent heater is a cross process exchanger, wherein the C9-effluent heater is configured to transfer heat from the transalkylation effluent to the mixed transalkylation feed.

6. The method of claim 1, wherein the effluent-transalkylation exchanger is a cross process exchanger, wherein the effluent-transalkylation exchanger is configured to transfer heat from the cooled transalkylation effluent to the separated transalkylation effluent.

7. The method of claim 1, wherein the dealkylation temperature is between 200° C. and 500° C., wherein the dealkylation pressure is between 5 bar and 40 bar, and wherein the liquid hourly space velocity in the dealkylation reactor is between 1 hr$^{-1}$ and 10 hr$^{-1}$.

8. The method of claim 1, wherein the transalkylation temperature is between 300° C. and 500° C., wherein the transalkylation pressure is between 10 bar and 40 bar, wherein the liquid hourly space velocity in the transalkylation reactor is between 0.5 hr$^{-1}$ and 6 hr$^{-1}$.

9. A method for producing mixed xylenes from a heavy reformate feed, the method comprising the steps of:
  introducing the heavy reformate feed to a feed exchanger to produce a hot feed stream, wherein the feed exchanger increases the temperature of the heavy reformate feed, wherein the heavy reformate comprises aromatic hydrocarbons with nine or more carbon atoms (C9+ aromatics), wherein the hydrogen feed comprises hydrogen gas; mixing the hot feed stream and a hydrogen feed to produce a mixed feed; increasing a temperature of the mixed feed in a feed cross exchanger to produce a heated mixed feed, wherein a temperature of the heated mixed feed is between 65° C. and 90° C.;
  increasing the temperature of the heated mixed feed in a feed-xylene exchanger to produce a warm mixed feed, wherein a temperature of warm mixed feed is between 90° C. and 150° C.;
  increasing the temperature of the warm mixed feed in a feed-effluent exchanger to produce a hot mixed feed, wherein a temperature of the hot mixed feed is between 324° C. and 344° C.;
  increasing the temperature of the hot mixed feed in a feed fired heater to produce a hot reactor feed, wherein a temperature of the hot reactor feed is between 380° C. and 400° C.;
  introducing the hot reactor feed to a dealkylation reactor, wherein the dealkylation reactor comprises a dealkylation catalyst;
  reacting the heavy reformats feed with the hydrogen gas in the presence of the dealkylation catalyst in the dealkylation reactor to produce a dealkylation effluent, wherein the dealkylation reactor is at a dealkylation temperature, wherein the dealkylation reactor is at a dealkylation pressure, wherein the dealkylation reactor has a liquid hourly space velocity;
  reducing a temperature of the dealkylation effluent in the feed-effluent exchanger to produce a cooled effluent stream, wherein a temperature of the cooled effluent stream is between 115° C. and 145° C.;
  reducing the temperature of the cooled effluent in an effluent-separator exchanger to produce an effluent stream, wherein the temperature of the effluent stream is between 80° C. and 110° C.;
  reducing the temperature of the effluent stream in the feed cross exchanger to produce a warm effluent, wherein a temperature of the warm effluent is between 65° C. and 80° C.;
  reducing the temperature of the warm effluent in an effluent cooler to produce a mixed effluent stream, wherein a temperature of the mixed effluent stream is between 38° C. and 47° C.;
  separating the mixed effluent stream in an effluent separator to produce a produced hydrogen and a separated effluent, wherein the produced hydrogen comprises hydrogen;
  increasing a temperature of the separated effluent in the effluent-separator exchanger to produce a dealkylation splitter feed, wherein a temperature of the dealkylation splitter feed is between 100° C. and 130° C.;
  introducing the dealkylation splitter feed to a splitter unit, where the dealkylation effluent comprises light gases, toluene, benzene, mixed xylenes, and C9+ aromatics;
  separating the dealkylation effluent into a light gas product, a toluene stream, a benzene stream, a C9 aromatics stream, a C10+ aromatics stream, and a mixed xylene stream in the splitter unit, wherein the light gas stream comprises light hydrocarbons and hydrogen, wherein the toluene stream comprises toluene, wherein the benzene stream comprises benzene, wherein the mixed xylene stream comprises mixed xylenes, wherein the C9 stream comprises C9 aromatics, wherein the C10+ aromatics stream comprises C10+ aromatics;
  mixing the toluene stream, the C9 aromatics stream, and a hydrogen stream in a mixer to produce a mixed transalkylation feed;
  increasing a temperature of the mixed transalkylation feed in a C9-effluent heater to produce a hot transalkylation feed, wherein a temperature of the hot transalkylation feed is between 330° C. and 390° C.;
  increasing a temperature of the hot transalkylation teed in a transalkylation fired heater to produce a transalkylation feed, wherein a temperature of the transalkylation feed is between 380° C. and 400° C.;
  introducing the transalkylation feed to a transalkylation reactor, wherein the transalkylation reactor comprises a transalkylation catalyst, wherein the hydrogen stream comprises hydrogen gas;
  reacting the toluene stream and the C9 aromatics stream in the presence of the transalkylation catalyst to produce a transalkylation effluent, wherein the transalkylation reactor is at a transalkylation temperature, wherein the transalkylation reactor is at a transalkylation pressure, wherein the transalkylation reactor has a liquid hourly space velocity;
  reducing a temperature of the transalkylation effluent in the C9-effluent heater to produce a cooled transalkylation effluent, wherein a temperature of the cooled transalkylation effluent between 136° C. and 166° C.;
  reducing the temperature of the cooled transalkylation effluent in an effluent-transalkylation exchanger to produce a cooled effluent, wherein a temperature of the cooled effluent is between 83° C. and 103° C.;
  reducing the temperature of the cooled effluent in the feed exchanger to produce a mixed effluent, wherein a temperature of the mixed effluent is between 45° C. and 78° C.; reducing the temperature of the mixed effluent in a transalkylation cooler to produce a cooled mixed effluent, wherein a temperature of the cooled mixed effluent is between 35° C. and 45° C.;
  separating the cooled mixed effluent in a transalkylation separator to produce a separated transalkylation effluent and a light gases stream; increasing a temperature of the separated transalkylation effluent in the effluent-transalkylation exchanger to produce a transalkylation splitter feed, wherein a temperature of the transalkylation splitter feed is between 105° C. and 125° C.;
  introducing the transalkylation splitter feed to the splitter unit, wherein the transalkylation effluent comprises light gases, toluene, benzene, mixed xylenes, and C9+ aromatics; separating the transalkylation splitter feed in the splitter unit such that mixed xylenes in the transalkylation splitter feed exit the splitter unit as part of the mixed xylene stream; reducing a temperature of the mixed xylene stream in the feed-xylene exchanger to produce a cooled xylene stream, wherein a temperature of the cooled xylene stream is between 55° C. and 65° C.; and reducing the temperature of the cooled xylene stream in a xylene cooler to produce a mixed xylene product, wherein a temperature of the mixed xylene product is between 30° C. and 50° C.

10. The method of claim 9, wherein the feed exchanger is a cross process exchanger, wherein the feed exchanger is configured to transfer heat from the mixed xylene stream to the heavy reformate feed.

11. The method of claim 9, wherein the feed cross exchanger is a cross process exchanger, wherein the feed cross exchanger is configured to transfer heat from the effluent stream to the mixed feed.

12. The method of claim 9, wherein the feed-xylene exchanger is a cross process exchanger, wherein the feed-xylene exchanger is configured to transfer heat from the mixed xylene stream to the heated mixed feed.

13. The method of claim 9, wherein the feed-effluent exchanger is a cross process exchanger, wherein the feed-effluent exchanger is configured to transfer heat from the dealkylation effluent to the warm mixed feed.

14. The method of claim 9, wherein the effluent-separator exchanger is a cross process exchanger, wherein the effluent-separator exchanger is configured to transfer heat from the cooled effluent stream to the separated effluent.

15. The method of claim 9, wherein the C9-effluent heater is a cross process exchanger, wherein the C9-effluent heater is configured to transfer heat from the transalkylation effluent to the mixed transalkylation feed.

16. The method of claim 9, wherein the effluent-transalkylation exchanger is a cross process exchanger, wherein the effluent-transalkylation exchanger is configured to transfer heat from the cooled transalkylation effluent to the separated transalkylation effluent.

17. The method of claim 9, wherein the dealkylation temperature is between 200° C. and 500° C., wherein the dealkylation pressure is between 5 bar and 40 bar, and wherein the liquid hourly space velocity in the dealkylation reactor is between 1 $hr^{-1}$ and 10 $hr^{-1}$.

18. The method of claim 9, wherein the transalkylation temperature is between 300° C. and 500° C., wherein the transalkylation pressure is between 10 bar and 40 bar, and wherein the liquid hourly space velocity in the transalkylation reactor is between 0.5 $hr^{-1}$ and 6 $hr^{-1}$.

* * * * *

UNITED STATES PATENT AND TRADEMARK OFFICE
CERTIFICATE OF CORRECTION

PATENT NO. : 10,252,958 B2  
APPLICATION NO. : 16/173412  
DATED : April 9, 2019  
INVENTOR(S) : Qi Xu et al.

Page 1 of 1

It is certified that error appears in the above-identified patent and that said Letters Patent is hereby corrected as shown below:

In the Claims

In Claim 1, Column 34, Line 32 the claim language reads: "introducing the transalkylation splitter teed to the;" - It should read: "introducing the transalkylation splitter feed to the;"

Signed and Sealed this  
Twenty-first Day of May, 2019

Andrei Iancu  
*Director of the United States Patent and Trademark Office*